US010583248B2

(12) United States Patent
Ohwada et al.

(10) Patent No.: US 10,583,248 B2
(45) Date of Patent: Mar. 10, 2020

(54) DROPLET MEASUREMENT SYSTEM, DROPLET MEASUREMENT METHOD AND COMPUTER READABLE RECORDING DEVICE

(71) Applicants: IGUNOSS, Inc., Iwate (JP); ICOMES LAB., Co., Ltd., Iwate (JP)

(72) Inventors: Isao Ohwada, Iwate (JP); Harumi Sangawa, Iwate (JP); Masatsugu Nitagai, Iwate (JP); Keiji Katano, Iwate (JP); Tadataka Kamiyama, Iwate (JP); Naoyuki Odashima, Iwate (JP)

(73) Assignees: ICOMES LAB, Co., Ltd., Iwate (JP); IGUNOSS, Inc., Iwate (JP)

( * ) Notice: Subject to any disclaimer, the term of this patent is extended or adjusted under 35 U.S.C. 154(b) by 55 days.

(21) Appl. No.: 15/911,914

(22) Filed: Mar. 5, 2018

(65) Prior Publication Data
US 2018/0256817 A1 Sep. 13, 2018

(30) Foreign Application Priority Data
Mar. 9, 2017 (JP) .................................. 2017-045479

(51) Int. Cl.
*A61M 5/168* (2006.01)
*A61M 5/172* (2006.01)
(Continued)

(52) U.S. Cl.
CPC .......... *A61M 5/16886* (2013.01); *A61M 5/14* (2013.01); *A61M 5/1411* (2013.01);
(Continued)

(58) Field of Classification Search
CPC .. A61M 2205/3306; A61M 2205/3379; A61M 2205/50; A61M 5/1411;
(Continued)

(56) References Cited

U.S. PATENT DOCUMENTS

2012/0095433 A1* 4/2012 Hungerford ........ A61M 5/1689
604/500
2013/0085443 A1 4/2013 Lowery et al.
2017/0304535 A1 10/2017 Hirata et al.

FOREIGN PATENT DOCUMENTS

JP 2011-062371 A 3/2011
JP 2016-518875 A 6/2016
(Continued)

*Primary Examiner* — Phillip A Gray
(74) *Attorney, Agent, or Firm* — Norris McLaughlin, P.A.

(57) ABSTRACT

A droplet measurement system is provided with: an imaging device placed to locate a tip part of a nozzle and the entire liquid hanging down from the nozzle within a field of view; an image generation unit that generates a plurality of images that capture the state in which droplets are dripping down from the nozzle based on image data output from the imaging device; a dripping detection unit that detects, from the plurality of images, a dripping-detected image in which the fact that a droplet has departed from the nozzle is detected; and a volume calculation unit that calculates the volume of the droplet based, at least, on an image-before-dripping, which is generated a predetermined number of frames before the dripping-detected image and capturing liquid hanging down from the nozzle and on a reference image that captures at least the tip part of the nozzle.

14 Claims, 16 Drawing Sheets

(51) Int. Cl.
*A61M 5/14* (2006.01)
*G06T 7/62* (2017.01)

(52) U.S. Cl.
CPC ........ *A61M 5/16804* (2013.01); *A61M 5/172* (2013.01); *G06T 7/62* (2017.01); *A61M 2205/3327* (2013.01); *A61M 2205/502* (2013.01); *A61M 2205/52* (2013.01); *G06T 2207/10016* (2013.01)

(58) Field of Classification Search
CPC ............ A61M 5/16804; A61M 5/1684; A61M 5/1689; A61M 5/16886; A61M 5/14; A61M 5/172
USPC .......................................................... 604/67
See application file for complete search history.

(56) References Cited

FOREIGN PATENT DOCUMENTS

| | | |
|---|---|---|
| JP | 2017-015626 A | 1/2017 |
| WO | 2016/114264 A1 | 7/2016 |

\* cited by examiner

FIG.13
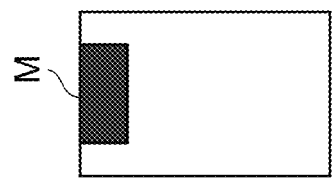
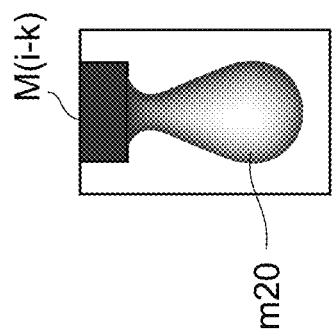

DROPLET MEASUREMENT SYSTEM, DROPLET MEASUREMENT METHOD AND COMPUTER READABLE RECORDING DEVICE

CROSS-REFERENCE TO RELATED APPLICATIONS

This application is based upon and claims the benefit of priority from Japanese Patent Application No. 2017-045479, filed on Mar. 9, 2017, the entire contents of which are incorporated herein by reference.

BACKGROUND OF THE INVENTION

Field of the Invention

The present invention relates to a droplet measurement system that measures the volume of droplets dripping down from a nozzle, a droplet measurement method and a computer readable recording device.

Description of the Related Art

It is important to maintain a predetermined flow rate when delivering liquid (infusion liquid), such as chemicals, nutritional supplements, or the like, intravenously. Conventionally, the infusion flow rate control has been performed by determining the number of drips per unit time by counting the number of droplets dripped in a drip tube, calculating the flow rate based on an assumption that the droplet volume is constant, and adjusting the dripping cycle of the droplets (i.e. the time interval of dripping).

However, in practice, the surface tension of the infusion liquid varies depending on the conditions, such as viscosity, ambient temperature, or the like, and thus, the volume per droplet is not constant. Moreover, in medical settings, patients may change their positions during infusion, and in such case, the head difference of the infusion liquid may change, and the volume of droplets may vary. Accordingly, the conventional method that controls the flow rate solely based on the dripping cycle of the droplets has been prone to errors in flow rate, and high-precision flow rate control has been difficult.

To handle such problems, a technique is known in which the volume of the dripping droplets is measured and used in the flow rate control. For example, JP2011-62371 A discloses a droplet detection device provided with: a transparent drip tube; a light emitting part arranged on one side of the exterior of the drip tube; and a two-dimensional image sensor arranged at a position opposite to the light emitting part with the drip tube sandwiched therebetween, wherein a field of view of the two-dimensional image sensor is set such that a tip of a dripping nozzle in the drip tube and a predetermined droppage distance of droplets dropping from the dripping nozzle are included.

When the volume of the droplets is calculated based on the general shape of the droplet during dropping, a two-dimensional image sensor is required which has a large size such that a range from the tip of the dripping nozzle to the predetermined droppage distance of droplets can be captured, and which also has a high frame rate. For this reason, the amount of image data to be processed increases, and thus, a sophisticated processing device is necessary that is capable of rapidly processing a large amount of arithmetic processing and memory operations in order to measure, substantially in real time, the volume of droplets that drip in succession. Consequently, the entire system configuration becomes extensive and the device cost increases. As a result, there is a possibility of it being difficult to mass-produce the system.

On the other hand, it is also possible to capture the range from the tip of the dripping nozzle to the predetermined droppage distance of droplets by making use of a general-purpose image sensor and by increasing the distance from the dripping nozzle to the image sensor. However, in this case, the size of the image of the droplet captured in the images decreases, and thus, the precision in calculating the volume of the droplets by means of image processing may be reduced. In addition, objects other than droplets can easily get captured in the images, and thus, there is a possibility for larger measurement errors to occur.

BRIEF SUMMARY OF THE INVENTION

An aspect of the present invention relates to a droplet measurement system. The droplet measurement system measures the volume of a droplet dripping down from a nozzle and includes: an imaging device that images a subject and outputs image data, wherein the imaging device is placed to locate a tip part of the nozzle and the entire liquid hanging down from the nozzle within a field of view; an image generation unit that generates, in a temporal sequential order, a plurality of images that capture the state in which droplets are dripping down from the nozzle based on the image data output from the imaging device; a dripping detection unit that detects, from the plurality of images generated in a temporal sequential order by the image generation unit, a dripping-detected image that is an image in which the fact that a droplet has departed from the nozzle is detected; and a volume calculation unit that calculates the volume of the droplet based, at least, on an image-before-dripping, which is an image generated, among the plurality of images, a predetermined number of frames before the dripping-detected image and capturing liquid hanging down from the nozzle and on a reference image, which is an image different from the image-before-dripping and is an image generated based on the image data output from the imaging device and capturing, at least, the tip part of the nozzle.

Another aspect of the present invention relates to a droplet measurement method. The droplet measurement method measures the volume of a droplet dripping down from a nozzle and includes: generating, in a temporal sequential order, a plurality of images that capture the state in which droplets are dripping down from the nozzle based on image data output from an imaging device that is placed to locate a tip part of the nozzle and the entire liquid hanging down from the nozzle within a field of view; detecting, from the plurality of images that are generated in a temporal sequential order and that capture the state in which droplets are dripping down from the nozzle, a dripping-detected image that is an image in which the fact that a droplet has departed from the nozzle is detected; and calculating the volume of the droplet based, at least, on an image-before-dripping, which is an image generated, among the plurality of images, a predetermined number of frames before the dripping-detected image and capturing liquid hanging down from the nozzle and on a reference image, which is an image different from the image-before-dripping and is an image generated based on the image data output from the imaging device and capturing, at least, the tip part of the nozzle.

A further aspect of the present invention relates to a computer readable recording device. The computer readable recording device stores thereon a program for measuring the volume of a droplet dripping down from a nozzle, and the program causes a computer to: generate, in a temporal sequential order, a plurality of images that capture the state in which droplets are dripping down from the nozzle based on image data output from an imaging device that is placed to locate a tip part of the nozzle and the entire liquid hanging down from the nozzle within a field of view; detect, from the plurality of images that are generated in a temporal sequential order and that capture the state in which droplets are drip down from the nozzle, a dripping-detected image that is an image in which the fact that a droplet has departed from the nozzle is detected; and calculate the volume of the droplet based, at least, on an image-before-dripping, which is an image generated, among the plurality of images, a predetermined number of frames before the dripping-detected image and capturing liquid hanging down from the nozzle and on a reference image, which is an image different from the image-before-dripping and is an image generated based on the image data output from the imaging device and capturing, at least, the tip part of the nozzle.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13 is a schematic diagram for describing the droplet volume calculation processing in a second embodiment of the present invention.

DETAILED DESCRIPTION OF THE INVENTION

The droplet measurement system, the droplet measurement method and the program according to embodiments of the present invention will be described hereinafter, with reference to the drawings. It should be noted that the present invention is not limited by these embodiments. In addition, in the descriptions of the respective drawings, identical parts are denoted by identical reference numbers.

The drawings to be referred to in the following description merely schematically show the shape, size and positional relationship to such an extent that the content of the present invention can be understood. Namely, the present invention is not limited to the shape, size and positional relationship illustrated in each drawing. Moreover, the drawings may include parts that differ in dimensional relationship or ratio among drawings.

First Embodiment

Figure 1:
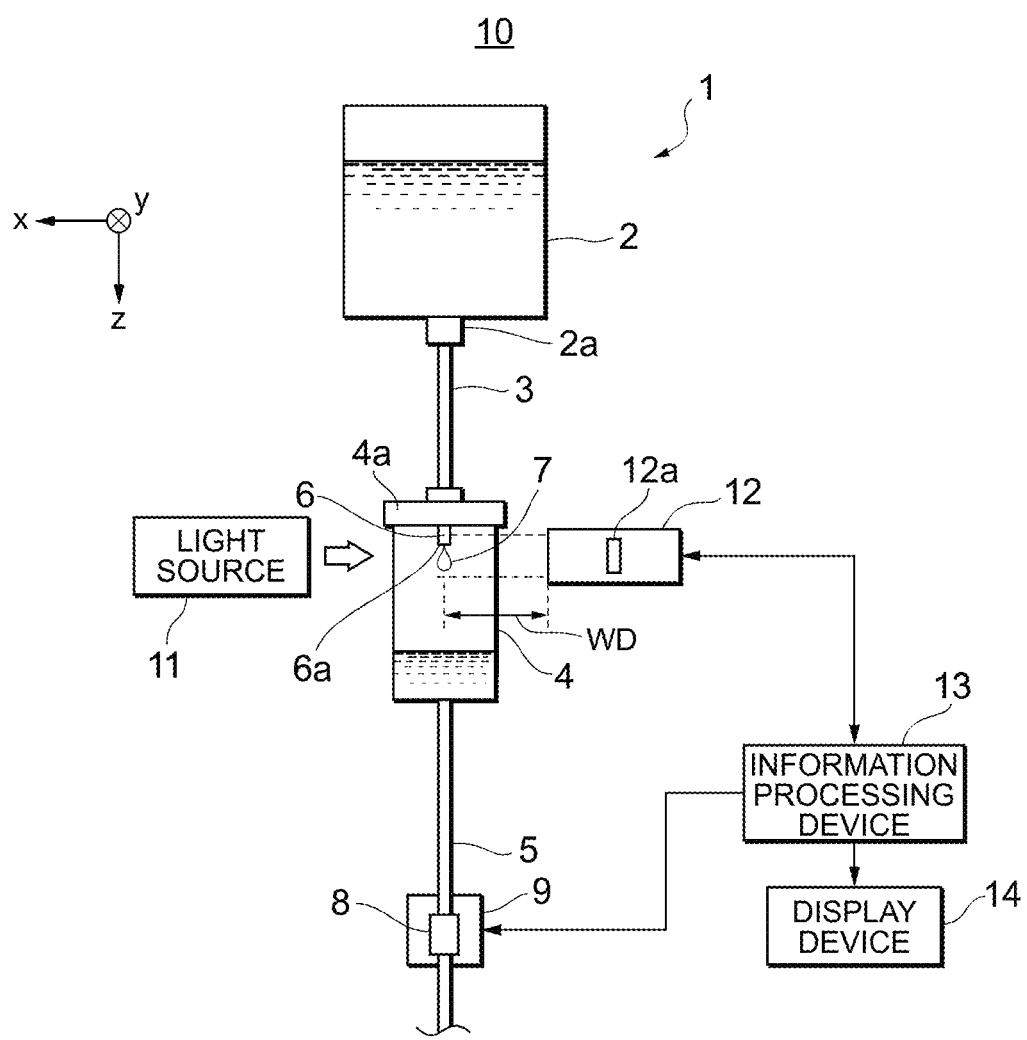
FIG. 1 is a diagram showing a schematic configuration of a droplet measurement system according to a first embodiment of the present invention.

FIG. 1 is a diagram showing a schematic configuration of a droplet measurement system according to a first embodiment of the present invention. As shown in FIG. 1, the droplet measurement system 10 according to the present embodiment is a system that measures the volume of droplets 7 dripping down from a tip 6a of a nozzle 6 (hereinafter also referred to as a nozzle tip) provided inside a drip tube 4 and that controls the flow rate of the infusion based on the measured volume, with respect to an infusion device 1 that supplies liquid (infusion liquid) filled in an infusion bag 2 via an intermediate tube 3, a drip tube 4 and an infusion tube 5.

The infusion bag 2 is a container filled with infusion liquid, such as chemicals, nutritional supplements, or the like, and is held in a suspended manner from a support, etc. during infusion. The intermediate tube 3 is connected, at one end thereof, to a drainage port 2a of the infusion bag 2 and is connected, at the other end thereof, to one end of the nozzle 6 that is attached to an upper lid 4a of the drip tube 4. The other end of this nozzle 6 is provided such as to project into the drip tube 4.

The infusion tube 5 is made of an elastic material. A clamp 8 that is capable of pressing the infusion tube 5 in a radial direction and an actuator 9 that drives the clamp 8 are provided in the midway of the infusion tube 5.

The actuator 9 varies the pressing force exerted by the clamp 8 with respect to the infusion tube 5 by driving the clamp 8 under the electrical control. By means of which the inner diameter of the infusion tube 5 changes (opens and closes), and then the flow rate of the infusion liquid that flows in the infusion tube 5 can be adjusted. Along with this, the internal pressure of the drip tube 4 changes and thus, the dripping cycle of the droplets 7 dripping down from the nozzle 6 changes.

The droplet measurement system 10 is further provided with a light source 11 that illuminates the drip tube 4, a camera 12 that images the interior of the drip tube 4 and generates image data, an information processing device 13 that calculates the volume of the droplets based on the image data generated by the camera 12, and a display device 14 that displays the result of the droplet volume calculations, or the like.

The light source 11 is provided with a light emitting element, for example, a light emitting diode (LED), or the like, and an optical system, such as a filter, a lens, or the like, that controls the light distribution such that the light output from the light emitting element becomes parallel light. The light source 11 is placed opposite to the field of view of the camera 12 and illuminates the neighborhood of the nozzle tip 6a, from which the droplets drip down, from behind the droplets 7.

The camera 12 includes an imaging element 12a, such as a charge coupled device (CCD), a complementary metal oxide semiconductor (CMOS), or the like, and is an imaging device capable of imaging a moving or still image at a predetermined imaging frame rate. The imaging element 12a receives light (subject image), at a light receiving surface thereof, that is incident on the camera 12 and that is image-formed by the optical system, and generates an electric signal by performing photoelectric conversion. The camera 12 generates and outputs image data by applying a predetermined signal processing, such as amplification, A/D conversion, etc., with respect to the electric signal.

The specifications of the camera 12 can be configured as appropriate, depending on the infusion device 1 being the target of measurement. As an example, when the infusion device 1 is a device generally used in the medical field, a compact camera may be preferably used with the size of the outer diameter of a camera module ranging from approximately a few millimeters to a few tens of millimeters and with the focus distance thereof ranging from approximately a few millimeters to a few tens of millimeters, such that the drip tube 4 can be imaged at close range and also such that the infusion operation by a user is not hindered.

As for the imaging element 12a, a general-purpose device with a total number of pixels being equal to or less than 500,000 can be used. More specifically, it may be sufficient if the number of pixels in the longer direction is in the approximate range of from 480 to 800 and the number of pixels in the shorter direction is in the approximate range of from 320 to 600 and if the aspect ratio is 1 or more. As described hereinafter, in the present embodiment, the camera 12 is placed such that the longer direction of the imaging element 12a is the vertical direction and the shorter direction thereof is the horizontal direction. Accordingly, in the following, the longer direction of the imaging element 12a will be referred to as the longitudinal direction and the shorter direction will be referred to the lateral direction.

It is preferable for the imaging frame rate of the camera 12 to be within a range of from 50 to 70 frames per second (fps). More preferably, the imaging frame rate may be variable within such range.

The camera 12 is placed so as to locate the nozzle tip 6a and a predetermined range below the nozzle tip 6a within the field of view. In particular, it is sufficient if the entire liquid hanging down from the nozzle tip 6a immediately before dripping is located within the field of view. At that time, the droplets in the process of dropping down after departing from the nozzle tip 6a may be partially or entirely out of the field of view. The size of the liquid hanging down from the nozzle tip 6a varies depending on the conditions, such as the nozzle diameter, the viscosity of the liquid, the dripping cycle, or the like, and thus, the range of the subject to be placed within the field of view of the camera 12 may preferably be determined by adjusting the work distance WD (distance between the subject and the lens tip of the camera 12). For example, when an adult nozzle is used for dripping 1 mL through 20 droplets, the size of the liquid hanging down becomes relatively large, and thus, the work distance WD may be longer. When an infant nozzle is used for dripping 1 mL through 60 droplets, the size of the liquid hanging down becomes relatively small, and thus, the work distance WD may be shorter.

Preferably, an object side telecentric lens may be provided on the camera 12. Here, the position and tilt of the nozzle 6 within the drip tube 4 may differ among individuals, and thus, even if a standard distance between the drip tube 4 and the camera 12 is determined, the actual work distance WD may vary. In such case, if light is made incident on the imaging element 12a via a commonly-used collective lens, the size of the subject image on the light-receiving surface of the imaging element 12a may vary and an error may occur in the processing of calculating the volume of the droplets 7. In contrast, if light is made incident on the imaging element 12a via the telecentric lens, even when the work distance WD varies, the variation in the size of the subject image on the light-receiving surface can be suppressed. It should be noted that an imaging side telecentric lens may be provided on the camera 12; however, this is not necessary.

Figure 2:
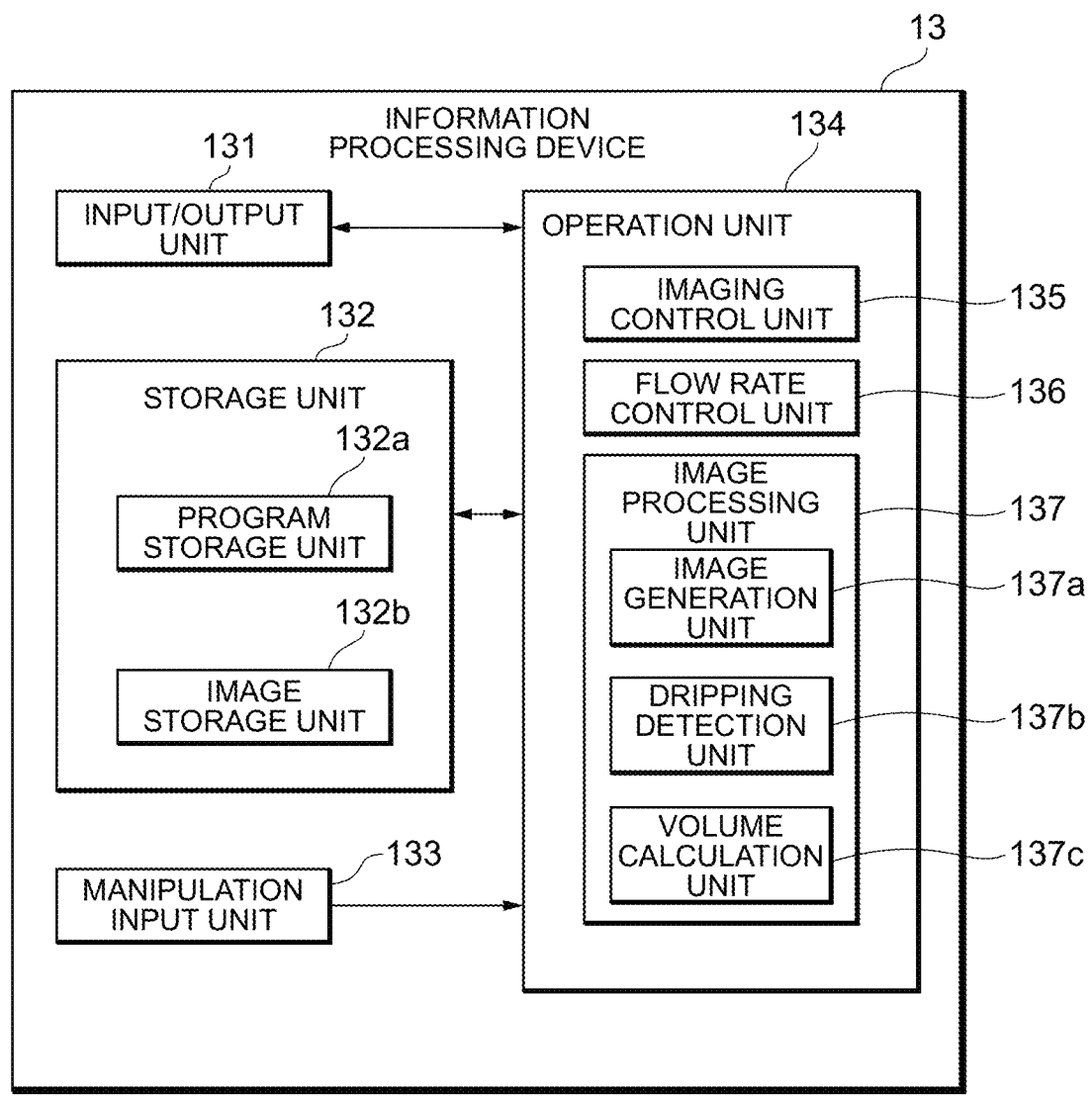
FIG. 2 is block diagram showing a schematic configuration of an information processing device shown in FIG. 1.

FIG. 2 is a block diagram showing a schematic configuration of an information processing device 13. As for the information processing device 13, in addition to the devices configured solely for the droplet measurement system 10, general-purpose information processing devices, such as a personal computer (PC), a laptop, or the like, may be used. As shown in FIG. 2, the information processing device 13 is provided with an input and output unit 131, a storage unit 132, a manipulation input unit 133 and an operation unit 134.

The input and output unit 131 is an external interface that performs input and output of image data or various signals among various external devices, such as the camera 12, the display device 14, and the like.

The storage unit 132 is configured with a computer readable storage medium, such as a semiconductor memory, such as a disk drive, a ROM, a RAM, or the like. The storage unit 132 stores therein, in addition to an operating system program and driver programs, programs for causing the information processing device 13 to execute predetermined operations, various types of data and configuration information, or the like, to be used during execution of the programs. More specifically, the storage unit 132 includes a program storage unit 132a that stores therein a droplet measurement program for measuring the volume of droplets 7 dripping down from the nozzle 6 and an image storage unit 132b that stores therein images generated based on the image data output from the camera 12.

The manipulation input unit 133 is configured with an input device, such as an input button, a switch, a keyboard, a mouse, a touch panel, or the like, and inputs signals according to the manipulations made by a user into the operation unit 134.

The operation unit 134 is configured with hardware, such as a central processing unit (CPU), a graphics processing unit (GPU), a digital signal processor (DSP), or the like, and it performs data transfer and instruction to the respective units of the information processing device 13 by reading and executing the programs stored in the program storage unit 132a and integrally controls the operation of the information processing device 13. In addition, the operation unit 134 executes the droplet measuring program stored in the program storage unit 132a to execute the arithmetic processing for calculating the volume of the droplets 7 dripping from the nozzle 6 based on the image data acquired from the camera 12. More specifically, functional parts that are realized by the operation unit 134 executing the droplet measuring program include an imaging control unit 135, a flow rate control unit 136 and an image processing unit 137.

The imaging control unit 135 controls the beginning and ending of imaging by the camera 12 as well as the operation of the camera 12 to carry out imaging at a predetermined imaging frame rate. The imaging control unit 135 may also perform control for limiting the imaging area of the imaging element 12a. For example, with respect to the imaging element 12a having 800×600 pixels, the effective imaging area may be variably set in the range of (480 to 800)×(320 to 600) pixels, and the imaging control unit 135 may perform control such that image signals are acquired only from those pixels arranged within the set imaging area. In this way, the load of processing the image signals can be reduced while the entire liquid hanging down from the nozzle 6 is placed within the field of view, regardless of the conditions, such as the nozzle diameter, the viscosity of the infusion liquid, the dripping cycle, or the like, by making the imaging area variable.

The flow rate control unit 136 controls the operation of the actuator 9 based on the volume of the droplets 7 calculated in the below-described image processing unit 137. Here, the flow rate of the infusion liquid can be obtained by dividing the volume of the droplet 7 by the dripping cycle of the droplets 7. The flow rate control unit 136 retains therein a target flow rate predetermined by a user and performs control such that the actual flow rate approaches this target flow rate.

The image processing unit 137 includes an image generation unit 137a, a dripping detection unit 137b and a volume calculation unit 137c, and performs predetermined processing on the image data input from the camera 12. More specifically, the image generation unit 137a generates images by applying predetermined image processing on the input image data, such as demosaicing, white balance processing, gamma correction, or the like. The dripping detection unit 137b detects, from the images generated by the image generation unit 137a, an image that captures the state immediately after the droplet 7 dripped down from the nozzle 6. The volume calculation unit 137c calculates the volume of the droplets 7 dripping down from the nozzle 6 based on the images generated by the image generation unit 137a and the detection result of the image by the dripping detection unit 137b.

It should be noted that the hardware configuration of the operation unit 134 is not limited to that described above and that the respective function configurations of the operation unit 134 may be realized with circuits, such as a field programmable gate array (FPGA), or the like.

The display device 14 is configured by a liquid crystal display, an organic EL display, or the like, and displays control signals output from the information processing device 13, the images generated by the information processing device 13, or the like, under the control of the information processing device 13.

Figure 3:
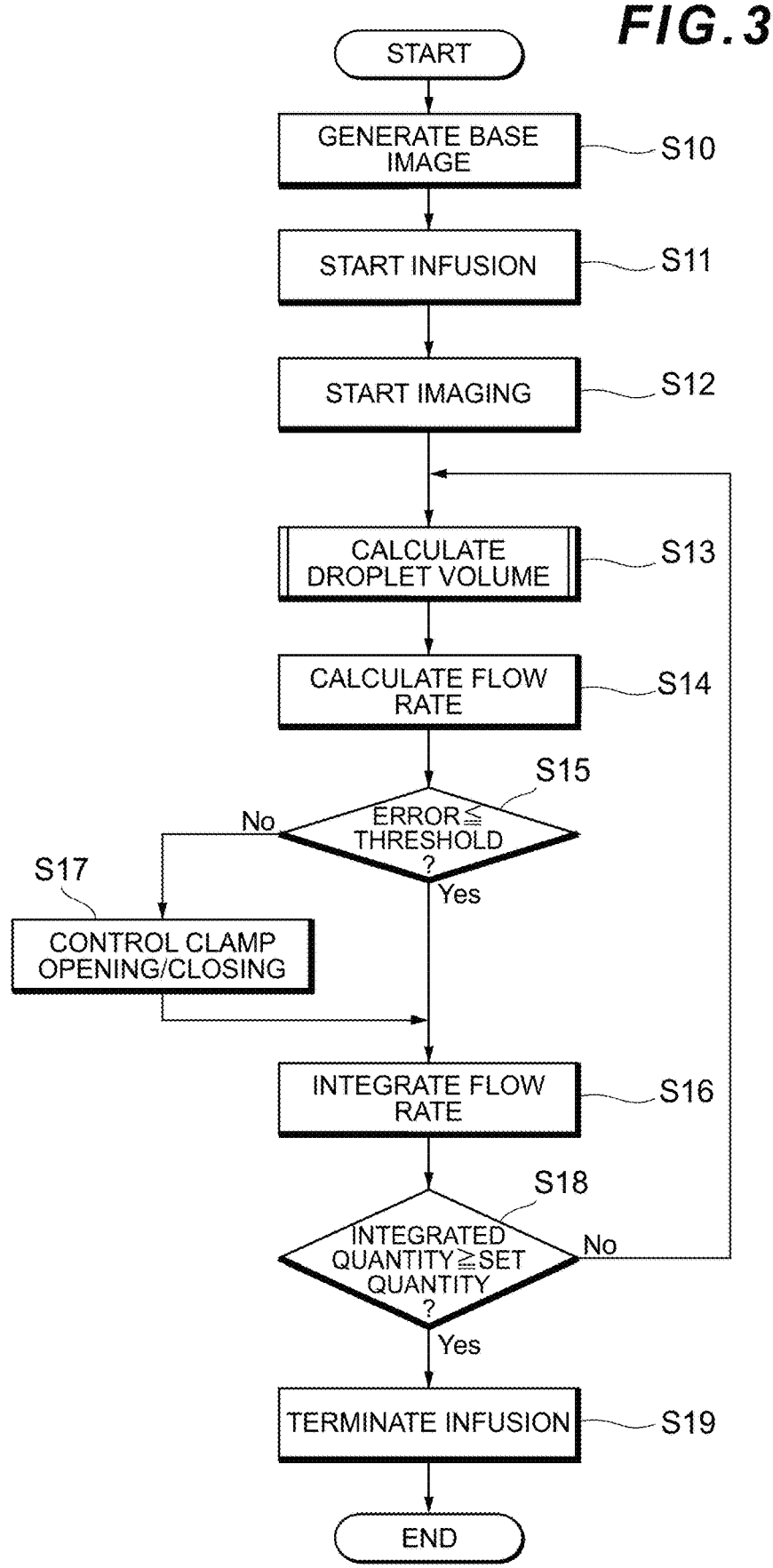
FIG. 3 is a flowchart showing the operations of the droplet measurement system shown in FIG. 1.

Next, the operation of the droplet measurement system 10 will be described. FIG. 3 is a flowchart illustrating the operation of the droplet measurement system 10.

Before starting infusion, a user places the light source 11 and the camera 12 in the neighborhood of the drip tube 4 (see FIG. 1). At this time, an image imaged by the camera 12 is displayed on the display device 14. While checking the image, the positional relationship among the light source 11, the drip tube 4 and the camera 12 is adjusted such that the nozzle tip 6a and the predetermined range below the nozzle tip 6a are located within the field of view of the imaging element 12a. In this situation, the user manipulates the information processing device 13 and causes the camera 12 to perform imaging.

In step S10, the image processing unit 137 of the information processing device 13 generates an image that captures the state before starting infusion, namely, an image that captures the state where no droplets 7 are dripped from the nozzle tip 6a, based on the image data input from the camera 12. Hereinafter, the image that captures the nozzle tip 6a in the state before starting infusion will be referred to as the base image. One base image is sufficient and the image processing unit 137 saves the generated base image in a memory. In the present embodiment, this base image is used as a reference image.

In step S11, the infusion operation in the infusion device 1 is started by driving the actuator 9 and by causing the clamp 8 to open the infusion tube 5 under the control of the flow rate control unit 136.

Figure 4:
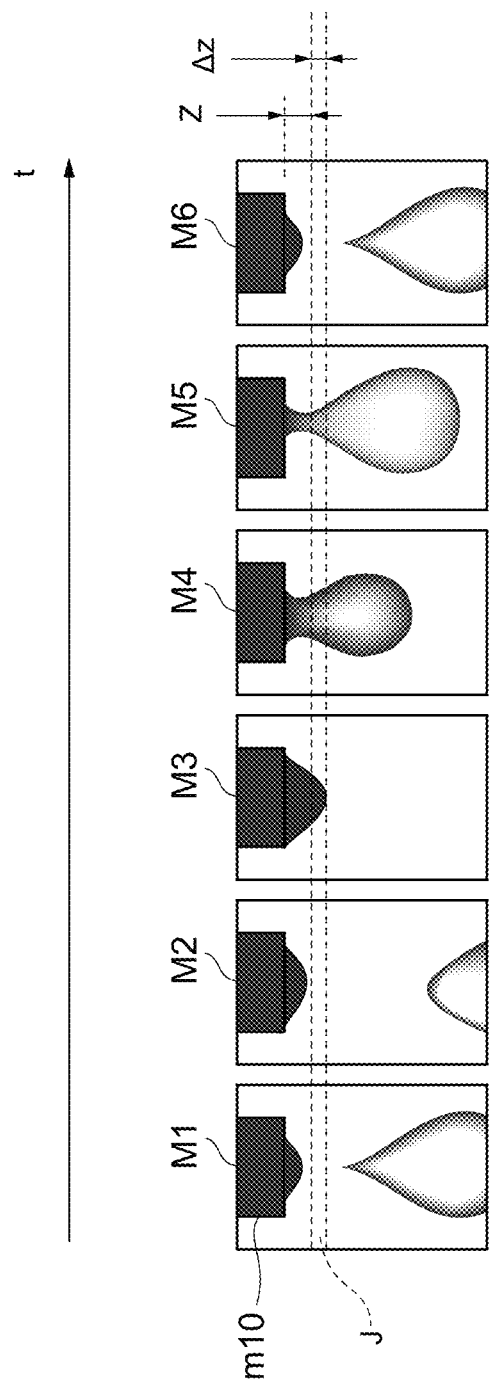
FIG. 4 is a schematic diagram illustrating images generated by an image generation unit shown in FIG. 2 in a temporal sequence order.

In the subsequent step S12, the imaging control unit 135 causes the camera 12 to start imaging at a predetermined imaging frame rate. In response thereto, the image generation unit 137a generates, in a temporal sequence order, images that capture the state in which the droplets 7 drip down from the nozzle tip 6a based on the image data sequentially input from the camera 12. FIG. 4 is a schematic diagram showing the images in the temporal sequence order generated by the image generation unit 137a. Hereinafter, the direction in which the droplet image moves in the images in the temporal sequence order will be referred to as the downward direction.

The image m10 of the nozzle captured in images M1 to M6 shown in FIG. 4 represents the tip part of the nozzle 6 shown in FIG. 1. The images M1 and M2 show part of a droplet that drops down after departing from the nozzle 6 and a liquid accumulation started to be formed at the tip part of the nozzle 6. In the images M3, M4 and M5, the dropping-down droplet has disappeared from the field of view, and such images show the state in which the liquid accumulation at the tip part of the nozzle 6 is gradually growing. The image M6 shows the state in which the grown liquid accumulation has departed from the nozzle 6 and is dropping down as a droplet. Hereinafter, the parameter that represents the order of image generation will be denoted as i, and thus, the image generated in the $i^{th}$ order will be denoted as the image M(i).

Figure 5:
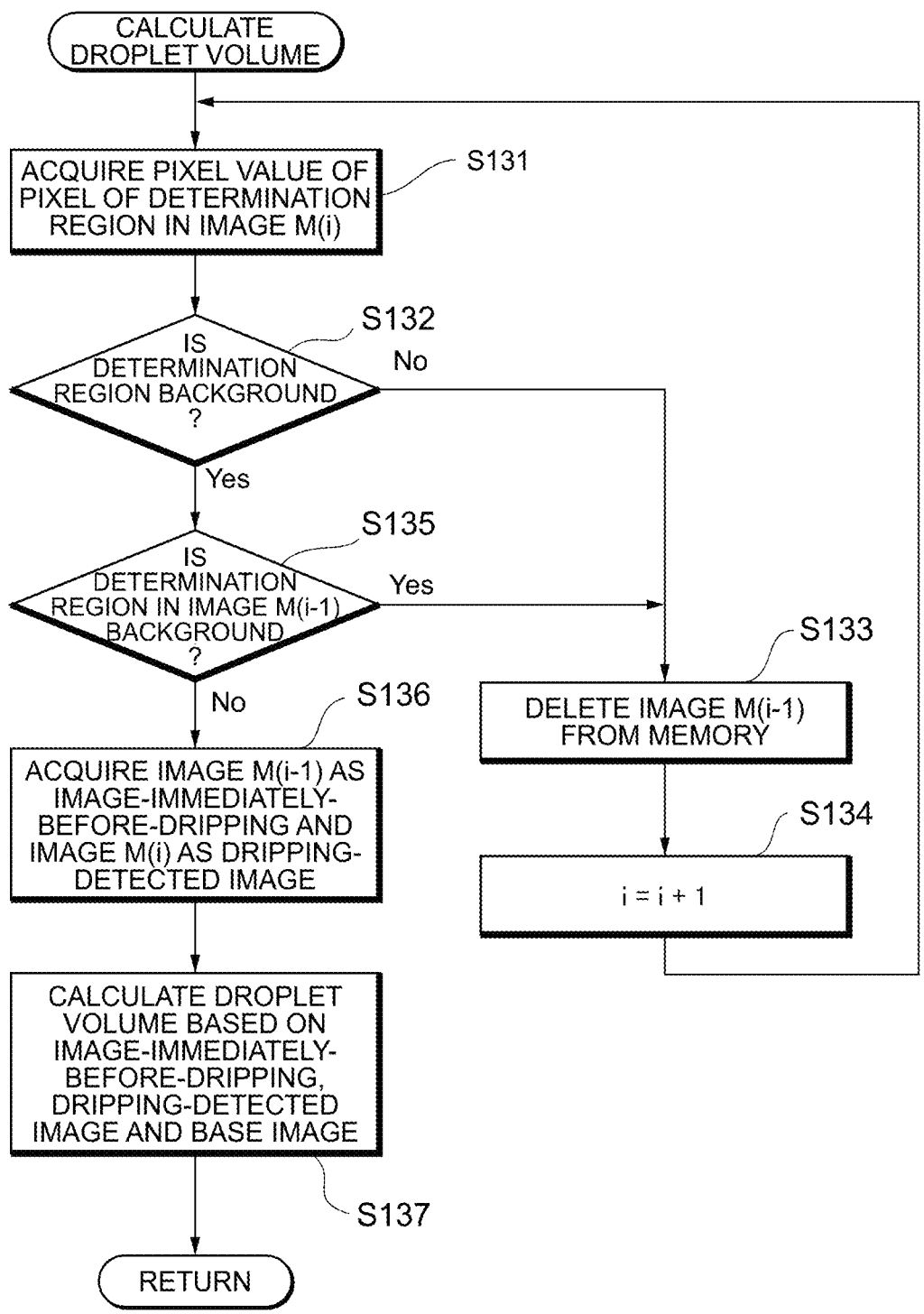
FIG. 5 is a flowchart showing a droplet volume calculation processing in the first embodiment of the present invention.

In the subsequent step S13, the image processing unit 137 calculates the volume of the droplet 7. FIG. 5 is a flowchart illustrating a process of calculating the volume of the droplets 7.

In step S131, the dripping detection unit 137b extracts, from the latest image M(i) generated in step S131, a pixel value of a pixel contained in a region J having a width Δz located at a position separated from the tip part of the nozzle image m10 by a predetermined distance (number of pixels) Z. The region J is set at the position where the liquid is cut off when the grown liquid accumulation departs from the nozzle and drips down as a droplet. The distance Z varies depending on the diameter of the nozzle 6 used, the viscosity of the liquid, the dripping cycle, the work distance WD, or the like, and thus, it may be set based on the image acquired, for example, at the time when an infusion test was conducted in advance. In addition, the width Δz is a width corresponding to one to several pixels.

In the subsequent step S132, the dripping detection unit 137b determines whether the determination region J is the background. Here, a background refers to a region in which no liquid, being the subject, is captured. More specifically, the dripping detection unit 137b determines whether the luminance of each pixel contained in the determination region J is equal to or larger than a threshold, and the determination region J is determined to be the background when the luminance of all pixels contained in the determination region J is equal to or larger than the threshold. For example, the determination regions J in the images M1, M2 and M6 shown in FIG. 4 are determined to be the background (step S132: Yes), and the determination region J in the images M3, M4 and M5 are determined to not be the background (step S132: No).

When the determination region J is not the background (step S132: No), the dripping detection unit 137b deletes from the memory (step S133) the image M(i−1) that was acquired immediately before the image M(i), with respect to which the determination was made. Thereafter, the dripping detection unit 137b incrementally increases the parameter i (step S134), and the process proceeds to step S131.

On the other hand, when the determination region J is the background (step S132: Yes), the dripping detection unit 137b subsequently determines whether the determination region J in the image M(i−1) that was acquired immediately before the image M(i) is the background (step S135). For example, the determination region J in the image M1 immediately before the image M2 shown in FIG. 4 is the background (step S135: Yes). On the other hand, the determination region J in the image M5 immediately before the image M6 is not the background (step S135: No).

When the determination region J in the image M(i−1) immediately before the image M(i) is the background (step S135: Yes), the process proceeds to step S133.

On the other hand, when the determination region J in the image M(i−1) is not the background (step S135: No), the dripping detection unit 137b determines that a droplet 7 has departed and dripped down from the nozzle 6 (see FIG. 1) in the temporal neighborhood of the time when the image M(i−1) was imaged, and acquires the image M(i−1) as the image-immediately-before-dripping and the image M(i) as the dripping-detected image (step S136).

In the subsequent step S137, the volume calculation unit 137c calculates the volume of the droplet 7 based on the image-immediately-before-dripping, the dripping-detected image and the base image. FIGS. 6 to 10 are schematic diagrams for describing the process of calculating the volume of the droplet 7.

Here, as shown in FIG. 4, when observing the images generated in a temporal sequence order, a constriction formed in the droplet hanging down from the nozzle gradually becomes thin (see the images M4 and M5), the liquid is cut off at the constriction part, and the part below the constriction drops down as a droplet (see the image M6). At this time, the part above the constriction remains attached to the nozzle. Accordingly, the volume of the liquid hanging down from the nozzle immediately before the droplet drops down (see the image M5) is substantially equal to the sum of the volume of the liquid that remains on the nozzle when the droplet drops down (see the image M6) and the volume of the droplet in the course of dropping down.

Figure 6:
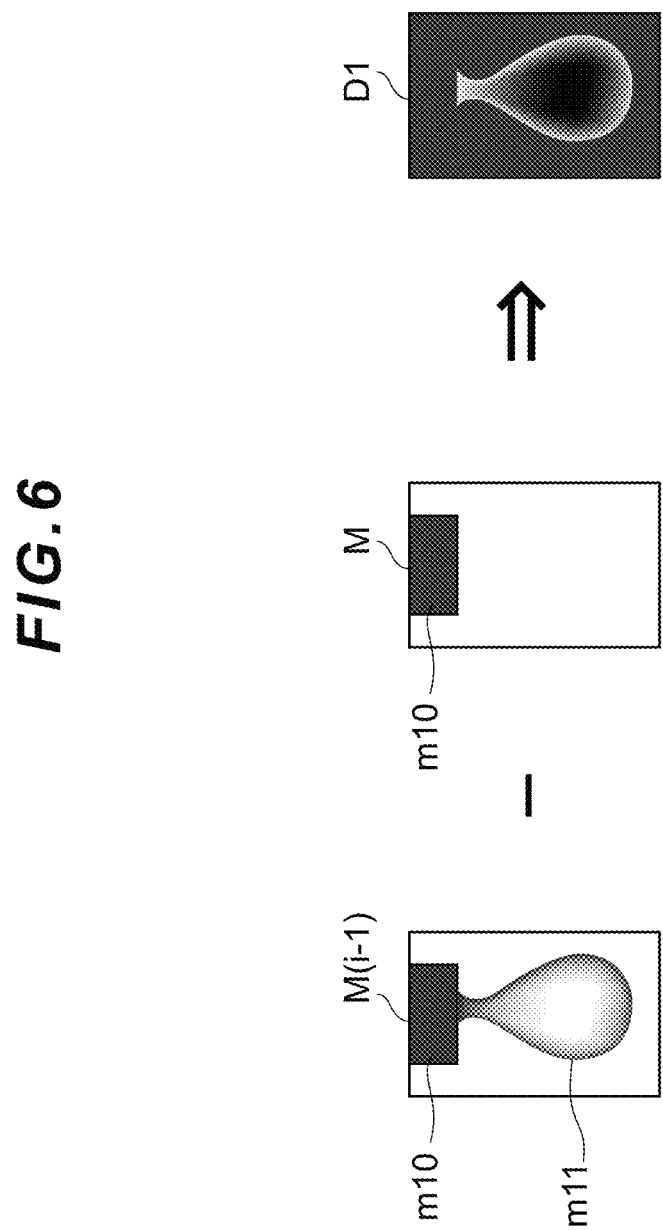
FIG. 6 is a schematic diagram for describing the droplet volume calculation processing.
Figure 7:
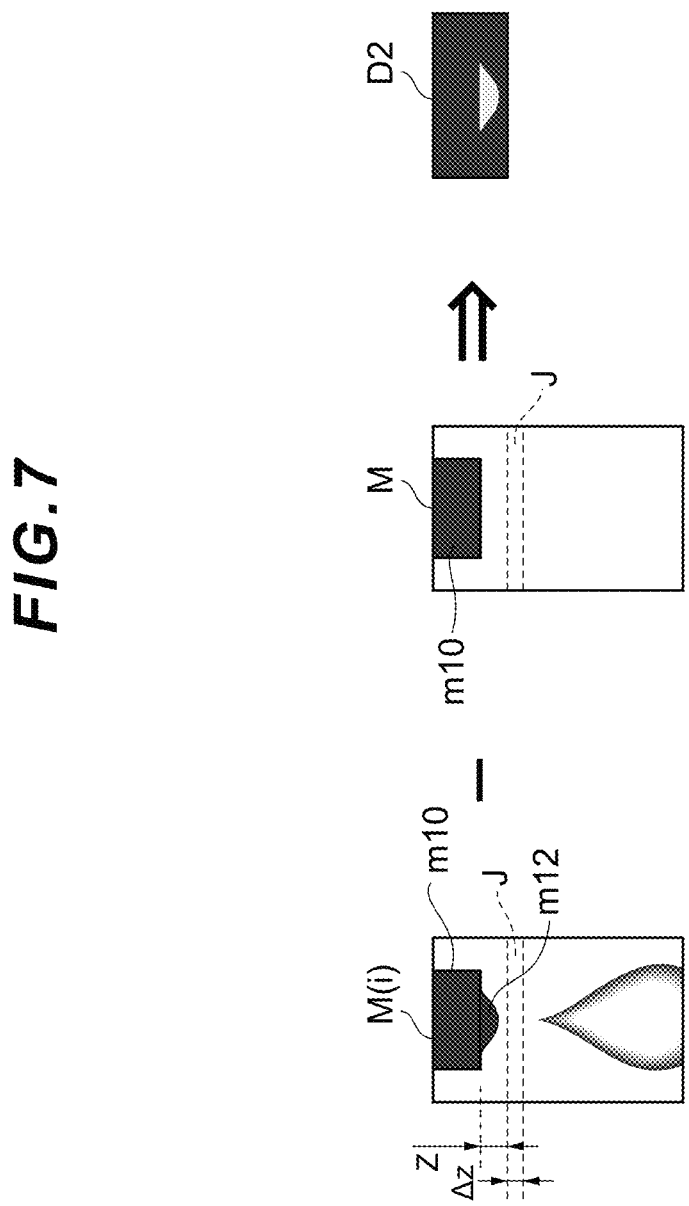
FIG. 7 is a schematic diagram for describing the droplet volume calculation processing.

Therefore, the volume calculation unit 137c acquires the image-immediately-before-dripping M(i−1), the dripping-detected image M(i) and the base image M, as shown in FIGS. 6 and 7, and calculates the volume of the droplet dripped down from the nozzle based on these images. More specifically, first, as shown in FIG. 6, a difference image D1 is created between the image-immediately-before-dripping M(i−1) and the base image M. The area of the image m11 of the liquid hanging down from the nozzle is extracted by applying binarization processing on the difference image D1. Then, the extracted area of the image m11 of the liquid is considered as a projection image of the liquid hanging down from the nozzle, and the volume V1 of a body of revolution is calculated, which is obtained by rotating the area of the image m11 of the liquid around the vertical axis.

The volume calculation unit 137c also creates, as shown in FIG. 7, a difference image D2 between the dripping-detected image M(i) and the base image M. The area of the image m12 of the liquid remaining on the nozzle is extracted by applying binarization processing on the difference image D2. When creating the difference image D2, the image of the droplet dropping down from the nozzle may be removed from the dripping-detected image M(i) by deleting, in advance, the area that is separated from the tip part of the image m10 of the nozzle by more than the predetermined distance. In particular, the area separated from the tip part of the image m10 of the nozzle by the distance Z or more than the distance Z+Δz may be deleted. Then, the volume calculation unit 137c presumes the extracted area of the image m12 of the liquid as a projection image of the liquid remaining on the nozzle, and the volume V2 of a body of revolution is calculated, which is obtained by rotating the area of the image m12 of the liquid around the vertical axis.

Moreover, the volume calculation unit 137c outputs the value obtained by subtracting the volume V2 that is calculated based on the image m12 of the liquid remaining on the nozzle from the volume V1 that is calculated based on the image m11 of the liquid hanging down from the nozzle, as the volume V3 of the droplet dropping down from the nozzle. It should be noted that, after calculating the volume V3, or before or after calculating the volumes V1 and V2, a calibration that transforms the volume calculated based on the object within the images to the actual scale may be performed.

Figure 8:
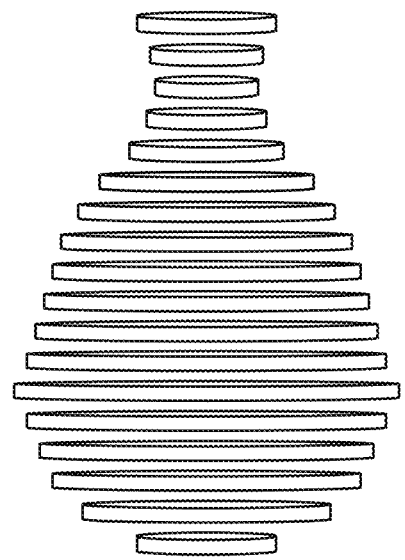
FIG. 8 is a schematic diagram for describing the droplet volume calculation processing.

The method of calculating the volumes V1, V2 of the bodies of revolution is not particularly limited. For example, each of the liquid hanging down from the nozzle and the liquid remaining on the nozzle may be considered as a body of revolution around one rotational axis, and then an integration operation may be performed based on each area of the liquid images m11 and m12. Alternatively, as shown in FIG. 8, each of the liquid hanging down from the nozzle and the liquid remaining on the nozzle may be considered as an object in which a plurality of disks, which are formed by slicing the liquid through the surfaces orthogonal to the axis in vertical direction, are stacked on top of each other, and then the volumes of cylinders may be integrated, the cylinders having a diameter corresponding to the width (i.e. the length in the horizontal direction) of the bar obtained by slicing each of the liquid images m11 and m12 at the predetermined height (e.g. 1 pixel).

Figure 9:
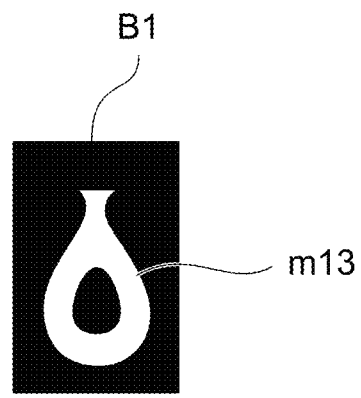
FIG. 9 is a schematic diagram for describing the droplet volume calculation processing.
Figure 10:
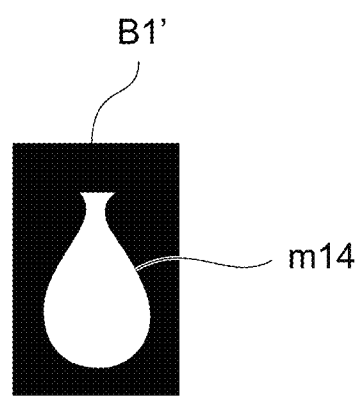
FIG. 10 is a schematic diagram for describing the droplet volume calculation processing.

Before the calculation of the volumes V1 and V2, the volume calculation unit 137c may also perform filling processing on the areas extracted by applying the binarization processing on the difference images D1 and D2. Here, a droplet located between the light source 11 and the camera 12 substantially directly transmits therethrough the light entering the center of such droplet and largely refracts and scatters the light entering the periphery of such droplet, as if such droplet was a convex lens. In the present embodiment, the area of the droplet image is extracted by detecting the contour formed by the light refracting and scattering at the periphery of the droplet. Accordingly, for example, as shown in FIG. 9, in the binary image B1, which is obtained by applying the binarization processing to the difference image D1, the area m13 corresponding to the droplet image m11 is extracted; however, the area corresponding to the lighter parts close to the center part of the droplet image m11 fails to appear. Then, the volume calculation unit 137c performs, on the extracted area m13, the filling processing (isolation point removal processing) that utilizes a publicly-known approach, such as morphology processing. The volume calculation unit 137c performs blob processing on the thus-obtained binary image B1' (see FIG. 10) to extract the area m14 corresponding to the droplet image m11 as a lump, and performs arithmetic processing for volume conversion based on this area m14.

After calculating the volume of the droplets in this manner, the process returns to the main routine.

With reference to FIG. 3 again, in step S14 subsequent to step S13, the flow rate control unit 136 calculates the current flow rate of the infusion liquid by dividing the volume of the droplet 7 calculated in step S13 by the dripping cycle.

In step S15, the flow rate control unit 136 determines whether the error between the current flow rate calculated in step S14 and the predetermined target flow rate is equal to or less than a threshold. This threshold may be predetermined according to the purpose of infusion. It should be noted that, at this point, a determination may be made as to whether the current flow rate and the target flow rate are equal.

When the error is determined to be equal to or less than the threshold (step S15: Yes), the flow rate control unit 136 integrates the current flow rate in a memory (step S16). Thereby, the integrated quantity of the flow rate will be updated.

On the other hand, when the error between the current flow rate and the target flow rate is determined to be larger than the threshold (step S15: No), the flow rate control unit 136 performs opening/closing control of the clamp 8 via the actuator 9 (step S17). In particular, when the current flow rate is larger than the target flow rate, control for closing the clamp 8 is performed and when the current flow rate is smaller than the target flow rate, control for opening the clamp 8 is performed. Thereafter, the process proceeds to step S16.

In step S18 subsequent to step S16, the flow rate control unit 136 determines whether the integrated quantity of the flow rate is equal to or larger than a predetermined set value (for example, of infusion amount). When the integrated quantity of the flow rate is determined to fail to satisfy the set value (step S18: No), the process returns to step S13.

On the other hand, when the integrated quantity of the flow rate is determined to be equal to or larger than the set value (step S18: Yes), the flow rate control unit 136 terminates the infusion (step S19) by causing the clamp 8 to block the infusion tube 5 via the actuator 9. Thereafter, the imaging control unit 135 shuts off the imaging operation by the camera 12. Accordingly, the operation of the droplet measurement system 10 terminates.

As described above, the first embodiment of the present invention calculates the volume of the droplets using: a dripping-detected image, in which the state where a droplet departs and drops down from the nozzle is detected; and an image-immediately-before-dripping, which captures the state, one frame prior to the dripping-detected image, in which the liquid is hanging down from the nozzle. Accordingly, it is no longer necessary to image the entire droplet that is dropping down from the nozzle with a high-spec camera with a large-sized imaging element and with a high frame rate, and a general-purpose camera 12 can be used.

In addition, according to the first embodiment of the present invention, the amount of data per image can be suppressed by reducing the size of the imaging element, and since only two images, namely, the image-immediately-before-dripping and the dripping-detected image, among the sequentially generated images are saved and processed, the arithmetic load and the load of memory operations in the information processing device 13 can be reduced. Accordingly, there is also no need to use a high-spec device for the information processing device 13. Therefore, the droplet measurement system 10 can be configured in a simple and cheap manner with a general-purpose camera 12 and a general-purpose information processing device 13, and thus, mass production may also be enabled.

Moreover, since the first embodiment of the present invention uses the liquid that remains hanging down from the nozzle 6 and the tip part thereof as the subject, the position of the subject is extremely stabilized. In particular, since the subject is always present on the center axis of the drip tube 4, the angle of view can be kept within a narrow range and the variations in the work distance WD can be suppressed. Here, in the drip tube 4, the droplet 7 dripping down from the nozzle 6 occasionally fails to drop down in the vertical direction and gets attracted to the wall surface of the drip tube 4 due to static electricity, etc. For this reason, when imaging the dropping droplet 7, the image size of the droplet 7 in the image may vary due to the variation in the work distance WD or the focus of the image of the droplet 7 may be blurred, and thus, there is a possible risk of the precision being affected in measuring the volume of the droplets 7. However, with the present embodiment, the liquid in the state of being attached to the nozzle 6 is imaged, and the volume of the droplets 7 can therefore be measured with good and stable precision regardless of the paths of the dropping droplets 7.

Furthermore, since the first embodiment of the present invention uses the liquid hanging down from the nozzle 6 and the tip part thereof as the subject, the illumination area of the light source 11 can be limited to a narrow range. Accordingly, a compact and cheap device can be used as the light source 11, and the space for placing the light source 11 can also be reduced to aim for electric power savings.

Moreover, since the first embodiment of the present invention feedback-controls the flow rate via the actuator 9 based on the calculation result of the volume of the droplets 7, a precise infusion can be performed.

Example 1-1

An experiment was conducted for verifying the accuracy of the volume calculation processing in the present embodiment: by dripping down the liquid from the nozzle and then calculating the volume of droplets (hereinafter also referred to as the calculated volume $V_C$) through the volume calculation processing (see FIGS. 5 to 7) in the first embodiment of the present invention; and by determining the real volume of the dripped droplet (hereinafter also referred to as the real volume $V_R$). As for the camera, a general-purpose product was used, provided with an imaging element of 640 pixels long and 480 pixels wide (approximately 300,000 pixels in total) and having an imaging frame rate of 60 fps.

The real volume $V_R$ was determined by collecting the dripped down droplet to measure the weight thereof, by dividing the weight with the number of droplets to calculate the weight per droplet, and by treating 1 g of droplet as 1 mL. The number of droplets to be collected was set as 20 or more per experiment.

The calculated volume $V_C$ was specifically calculated as described below. First, based on the area of the liquid image m11 illustrated in FIG. 6, the volume V1 of the liquid hanging down from the nozzle was calculated. In addition, based on the liquid image m12 illustrated in FIG. 7, the volume V2 of the liquid remaining on the nozzle was calculated. The volumes V1 and V2 were calculated, as shown in FIG. 8, by considering each area as an object in which cylinders with a height corresponding to one pixel are stacked on top of each other and by integrating the volumes of the cylinders. Then, the volume V2 was subtracted from the volume V1 to calculate volume $V_P$.

The thus-calculated volume $V_P$ is a volume (pixel$^3$/droplet) in the image space, and thus, calibration was conducted to convert this into the volume (μL/droplet) in the real space. The specific approach was as described below. Namely, the average $V_{R \cdot AVE}$ of the real volume $V_R$ (μL/droplet) and the average $V_{P \cdot AVE}$ of the volume $V_P$ (pixel$^3$/droplet) in the image space were calculated, and a calibration coefficient $C_0$ was calculated based on the following formula (1):

$$C_0 = V_{R \cdot AVE} / V_{P \cdot AVE} \quad (1)$$

The calculated volume $V_C$ was calculated, using the calibration coefficient $C_0$, based on the following formula (2):

$$V_C = C_0 \times V_P \quad (2)$$

Furthermore, using the average $V_{C \cdot AVE}$ of the calculated volume $V_C$, an error ratio shown in the following formula (3) was calculated, and the experiment result was evaluated based on this error ratio:

$$\text{Error ratio (\%)} = |V_{C \cdot AVE} - V_R| / V_R \times 100 \quad (3)$$

In the experiment, an infant nozzle for dripping 1 mL through 60 droplets (approx. 16.7 μL/droplet) was used and the infusion was performed by setting the work distance as 20 mm. A normal saline solution was used as the infusion liquid. The error ratio was calculated for each of the dripping cycles of 0.5 seconds/droplet, 1.0 second/droplet and 2.0 seconds/droplet. Thus, the following results were obtained:

Dripping cycle 0.5 seconds/droplet: error ratio 0.39%
Dripping cycle 1.0 second/droplet: error ratio 1.62%
Dripping cycle 2.0 seconds/droplet: error ratio 2.39%

As can be seen from the above, even when the volume is calculated based on the image of the liquid hanging down from the nozzle, comparable results can still be obtained to the substantive volume of the droplet dripped down from the nozzle.

Variation

Figure 11:
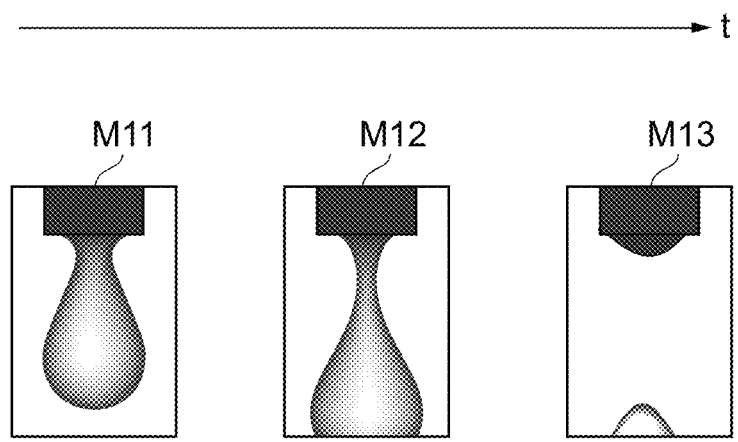
FIG. 11 is a schematic diagram for describing the droplet volume calculation processing in a variation of the first embodiment of the present invention.

Next, a variation of the first embodiment of the present invention will be described. FIG. 11 is a schematic diagram for describing the droplet volume calculation processing in the present variation.

Depending on the infusion conditions, such as the diameter of the nozzle used for the infusion, the viscosity of the liquid, the dripping cycle, or the like, and the imaging conditions, such as the work distance, or the like, the entire image of the liquid hanging down from the nozzle may not fit within the image-immediately-before-dripping M12 as shown in FIG. 11. As an example, when an adult nozzle for dripping 1 mL through 20 droplets (approx. 50 μL/droplet) is used to deliver a normal saline solution intravenously and when the work distance is set as 20 mm, part of the liquid hanging down from the nozzle runs off from the field of view in the image-immediately-before-dripping. In such case, as long as the entire liquid hanging down from the nozzle fits within the field of view, images of a few frames prior to the dripping-detected image M13 may be used, instead of the image-immediately-before-dripping M12, to calculate the volume of the droplets. Hereinafter, images acquired a predetermined number of frames prior to the dripping-detected image M13 are referred to as images before the dripping.

For example, in FIG. 11, the entire liquid hanging down from the nozzle fits within the field of view in the case of the image-before-dripping M11, which is an image acquired one frame before the image-immediately-before-dripping M12. In this case, using the image-before-dripping M11, instead of the image-immediately-before-dripping M12, the volume of the droplets can be calculated by means of image processing similar to that of the above-described first embodiment. Regarding the images before the dripping, preferably images acquired not more than four to five frames before the dripping-detected image M13, or more preferably images acquired not more than two to three frames before the dripping-detected image M13 may be used.

Example 1-2

The above-described adult nozzle was used, the work distance was set as 20 mm, the infusion was performed with other conditions being similar to those of Example 1-1, and the volume of the droplets was calculated by way of the volume calculation processing in the above-described variation. An image acquired two frames before the dripping-detected image was used as the image-before-dripping. Then, the following results were obtained when the error ratios were calculated in a manner similar to that of the above-described Example 1-1:

Dripping cycle 0.5 seconds/droplet: error ratio 4.84%
Dripping cycle 1.0 second/droplet: error ratio 1.93%
Dripping cycle 2.0 seconds/droplet: error ratio 7.18%

As can be seen from the above, even when the image-before-dripping, which is acquired two frames prior to the dripping-detected image, is used, the volume calculation result having a value relatively close to the real volume can still be obtained even there is a slight variation depending on the dripping cycle.

Reference Example

As a reference example, an experiment was conducted using a camera capable of capturing the entire droplet dripping from the nozzle, and the volume of the droplets was calculated based on the images in which the entire droplet was captured. As for the camera, a product was used provided with an imaging element of 1936 pixels long and 496 pixels wide and having an imaging frame rate of 120 fps.

Figure 12:
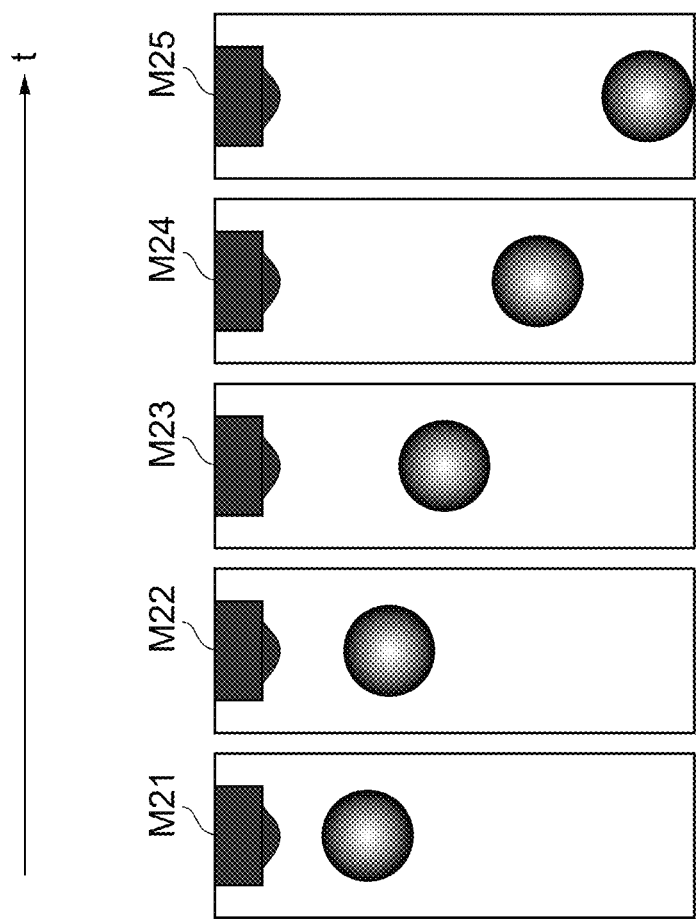
FIG. 12 is a schematic diagram for describing the droplet volume calculation processing in a reference example.

FIG. 12 is a schematic diagram for describing the droplet volume calculation processing in the reference example. When a camera provided with a large-sized imaging element is used and imaging is performed at a high frame rate, a plurality of images M21 to M25 that capture a droplet departed and dropping down from the nozzle can be acquired, as shown in FIG. 12. Then, for example, a difference image between the image M21 and the image M24 and a difference image between the image M21 and the image M25 are respectively calculated, and an area of one droplet within an image is extracted by further taking the difference between these difference images. This extracted area is considered to be the projection image of the droplet and the volume of the body of revolution formed by rotating the extracted area around the vertical axis is calculated as the volume of the droplet. The method of calculating the volume of the body of revolution may, as with the first embodiment, be a simple integration operation or a method of integrating the volumes of the disks as shown in FIG. 8.

In the experiment, the work distance was set as 20 mm, an adult nozzle and an infant nozzle were used, the infusion was performed with other conditions being similar to those of Example 1-1, and the volume of the droplets was calculated by means of the above-described method. Then, the following results were obtained when the error ratios were calculated in a manner similar to that of the above-described Example 1-1.

In the case of an adult nozzle and a work distance of 20 mm:
Dripping cycle 0.5 seconds/droplet: error ratio 0.84%
Dripping cycle 1.0 second/droplet: error ratio 0.10%
Dripping cycle 2.0 seconds/droplet: error ratio 0.92%
In the case of an infant nozzle and a work distance of 20 mm:
Dripping cycle 0.5 seconds/droplet: error ratio 1.44%
Dripping cycle 1.0 second/droplet: error ratio 0.12%
Dripping cycle 2.0 seconds/droplet: error ratio 1.90%
As can be seen from the above, a volume with little error with respect to the real volume can be calculated from the images in which the entire droplet is captured.

On the other hand, when the error ratios of the volumes calculated by Examples 1-1 and 1-2 are evaluated based on the error ratios of the volumes calculated by the reference example, it can be understood that generally comparable results to the reference example can be obtained for Example 1-1.

Second Embodiment

Next, a second embodiment of the present invention will be described. The droplet measurement system and the droplet measurement method according to the second embodiment of the present invention are generally similar to those of the above-described first embodiment (see FIGS. 1 to 3), and the droplet volume calculation processing in step S13 in FIG. 3 differs from that of the first embodiment. FIG. 13 is a schematic diagram for describing the droplet volume calculation processing in the second embodiment of the present invention.

Here, when comparing the above-described Example 1-2 to Example 1-1, Example 1-2 that used, as the image-before-dripping, an image acquired two frames before the dripping-detected image had, as a whole, a larger deviation from the real volume than Example 1-1 that used the image-immediately-before-dripping. Therefore, the images used for calculating the volumes that had a particularly large deviation from the real volume (i.e. the image-before-dripping and the dripping-detected image) among the images used in Example 1-2 were extracted and investigated. As a result, it was found that when, in the image-before-dripping, the liquid hanging down from the nozzle had not sufficiently grown and had a smaller volume than the average and when, in the dripping-detected image, the volume of the liquid remaining on the nozzle was larger than the average, the deviation from the real volume became large. Namely, it was found that an excessive volume tended to get subtracted as the liquid remaining on the nozzle from the volume of the liquid hanging down from the nozzle.

Thus, in the second embodiment of the present invention, the volume of the droplets is calculated using only the image-before-dripping and the base image (as a reference image). More specifically, as shown in FIG. 13, a difference image D3 is created by subtracting the base image M from the image-before-dripping M(i-k) (where k is an integer of 1 or more), which is an image acquired one or more frames before the dripping-detected image M(i). Then, the area of the image m20 of the liquid hanging down from the nozzle is extracted by applying the binarization processing and the filling processing on the difference image D3, and the volume of a body of revolution formed by rotating such area around the vertical axis is calculated as the volume of the droplet dripped down from the nozzle. The method of calculating the volume of the body of revolution may, as with the first embodiment, be a simple integration operation or a method of integrating the volumes of the disks as shown in FIG. 8. In addition, regarding the images before the dripping M(i-k), preferably, images acquired not more than four to five frames before the dripping-detected image M(i), more preferably, images acquired not more than two to three frames before the dripping-detected image M(i), or even more preferably, the image-immediately-before-dripping M(i−1) may be used on the condition that the entire liquid hanging down from the nozzle is within the field of view.

Example 2

An adult nozzle and an infant nozzle were used, the work distance was set as 20 mm, the infusion was performed with other conditions being similar to those of Example 1-1, and the volume of the droplets was calculated by way of the volume calculation processing in the second embodiment. Then, the following results were obtained when the error ratios were calculated in a manner similar to that of the above-described Example 1-1.

In the case of an adult nozzle and a work distance of 20 mm, and when an image acquired two frames before the dipping-detected image was used as an image-before-dripping:
Dripping cycle 0.5 seconds/droplet: error ratio 2.04%
Dripping cycle 1.0 second/droplet: error ratio 1.22%
Dripping cycle 2.0 seconds/droplet: error ratio 4.74%
In the case of an infant nozzle and a work distance of 20 mm, and when an image acquired one frame before the dip detection image was used as an image-before-dripping:
Dripping cycle 0.5 seconds/droplet: error ratio 0.51%
Dripping cycle 1.0 second/droplet: error ratio 1.62%
Dripping cycle 2.0 seconds/droplet: error ratio 2.51%
By comparing the experimental results in the case of the adult nozzle with the above-described Example 1-2, it can be seen that, in all of the dripping cycles, the error ratio is reduced, and the volume calculation precision has improved. In the case of the infant nozzle as well, it can be seen that comparable results to those of the above-described Example 1-1 are obtained.

Third Embodiment

Next, a third embodiment of the present invention will be described. The droplet measurement system and the droplet measurement method according to the third embodiment of the present invention are generally similar to those of the above-described first embodiment (see FIGS. 1 to 3), and the droplet volume calculation processing in step S13 in FIG. 3 differs from that of the first embodiment.

In the variation of the above-described first embodiment, when calculating the volume of the droplets using the image-immediately-before-dripping, the dripping-detected image and the base image, in the case where the entire image of the liquid hanging down from the nozzle does not fit within the image-immediately-before-dripping (see FIG. 11), an image acquired a few frames before the dripping-detected image was used instead of the image-immediately-before-dripping. However, the work distance may be varied in order to ensure a field of view with a sufficient angle of view such that the entire image of the liquid hanging down from the nozzle fits within the image-immediately-before-dripping. In this case, the volume of the droplets can be calculated by means of image processing similar to that of the first embodiment using the image-immediately-before-dripping, the dripping-detected image and the base image (see FIGS. 6 and 7).

Example 3

An adult nozzle and an infant nozzle were used, the work distance was set as 28 mm, the infusion was performed with other conditions being similar to those of Example 1-1, and the volume of the droplets was calculated by way of the volume calculation processing in the third embodiment. Then, the following results were obtained when the error ratios were calculated in a manner similar to that of the above-described Example 1-1.

In the case of an adult nozzle and the work distance of 28 mm, and when the volume was calculated based on the image-immediately-before-dripping, the dripping-detected image and the base image:
  Dripping cycle 0.5 seconds/droplet: error ratio 1.68%
  Dripping cycle 1.0 second/droplet: error ratio 0.79%
  Dripping cycle 2.0 seconds/droplet: error ratio 0.13%

In the case of an infant nozzle and a work distance of 28 mm, and when the volume was calculated based on the image-immediately-before-dripping, the dripping-detected image and the base image:
  Dripping cycle 0.5 seconds/droplet: error ratio 0.75%
  Dripping cycle 1.0 second/droplet: error ratio 0.37%
  Dripping cycle 2.0 seconds/droplet: error ratio 1.15%

By comparing the experimental results in the case of the adult nozzle with the above-described Example 1-2, it can be seen that, the volume calculation precision is improved as a whole when the volume is calculated using the image-immediately-before-dripping after adjusting the work distance such that the entire liquid hanging down from the nozzle fits within the image-immediately-before-dripping, as compared to when the volume is calculated using an image acquired two frames before the dripping-detected image. In the case of the infant nozzle as well, it can be seen that comparable results to those of the above-described Example 1-1 are obtained.

Fourth Embodiment

Next, a fourth embodiment of the present invention will be described. The droplet measurement system and the droplet measurement method according to the fourth embodiment of the present invention are generally similar to those of the above-described first embodiment (see FIGS. 1 to 3), and the droplet volume calculation processing in step S13 in FIG. 3 differs from that of the first embodiment.

In the above-described second embodiment, when calculating the volume of the droplets using the image-immediately-before-dripping and the base image, in the case where the entire image of the liquid hanging down from the nozzle does not fit within the image-immediately-before-dripping (see FIG. 11), an image acquired a few frames before the dripping-detected image was used instead of the image-immediately-before-dripping. However, the work distance may be varied in order to ensure a field of view with a sufficient angle of view such that the entire image of the liquid hanging down from the nozzle fits within the image-immediately-before-dripping. In this case, the volume of the droplets can be calculated by means of image processing similar to that of the second embodiment using the image-immediately-before-dripping and the base image (see FIG. 13).

Example 4

An adult nozzle and an infant nozzle were used, the work distance was set as 28 mm, the infusion was performed with other conditions being similar to those of Example 1-1, and the volume of the droplets was calculated by way of the volume calculation processing in the fourth embodiment. Then, the following results were obtained when the error ratios were calculated in a manner similar to that of the above-described Example 1-1.

In the case of an adult nozzle and a work distance of 28 mm, and when the volume was calculated based on the image-immediately-before-dripping and the base image:
  Dripping cycle 0.5 seconds/droplet: error ratio 0.25%
  Dripping cycle 1.0 second/droplet: error ratio 0.59%
  Dripping cycle 2.0 seconds/droplet: error ratio 1.19%

In the case of an infant nozzle and a work distance of 28 mm, and when the volume was calculated based on the image-immediately-before-dripping and the base image:
  Dripping cycle 0.5 seconds/droplet: error ratio 0.31%
  Dripping cycle 1.0 second/droplet: error ratio 0.37%
  Dripping cycle 2.0 seconds/droplet: error ratio 0.76%

By comparing the above-described experimental results with those of Example 2, it can be seen that, for both the adult nozzle and the infant nozzle, in all of the dripping cycles, the error ratio is reduced, and the volume calculation precision has improved.

Fifth Embodiment

Next, a fifth embodiment of the present invention will be described. The droplet measurement system and the droplet measurement method according to the fifth embodiment of the present invention are generally similar to those of the above-described first embodiment (see FIGS. 1 to 3), and the droplet volume calculation processing in step S13 in FIG. 3 differs from that of the first embodiment. FIGS. 14 to 17 are schematic diagrams for describing the droplet volume calculation processing in the fifth embodiment of the present invention.

In the above-described second embodiment, the area of the liquid hanging down from the nozzle was extracted from the difference image between the image-before-dripping and the base image. However, after starting infusion, as the time elapses, unnecessary droplets, etc. may get attached to the internal wall of the drip tube or to the nozzle and displacement may occur in the position or tilt of the nozzle. In such case, components unnecessary for droplet volume calculation cannot be cancelled out in the difference image between the image-before-dripping and the base image, and thus, there is a risk of the volume calculation precision affected.

Figure 14:
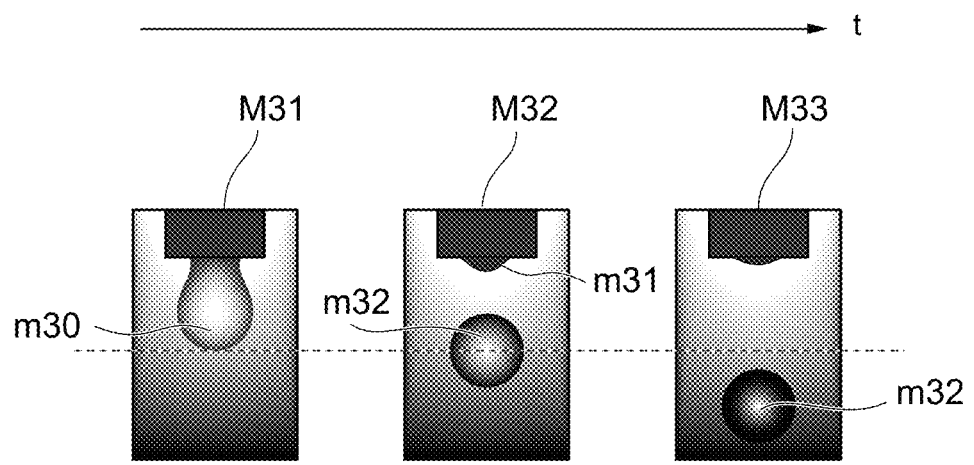
FIG. 14 is a schematic diagram for describing the droplet volume calculation processing in a fifth embodiment of the present invention.
Figure 15:
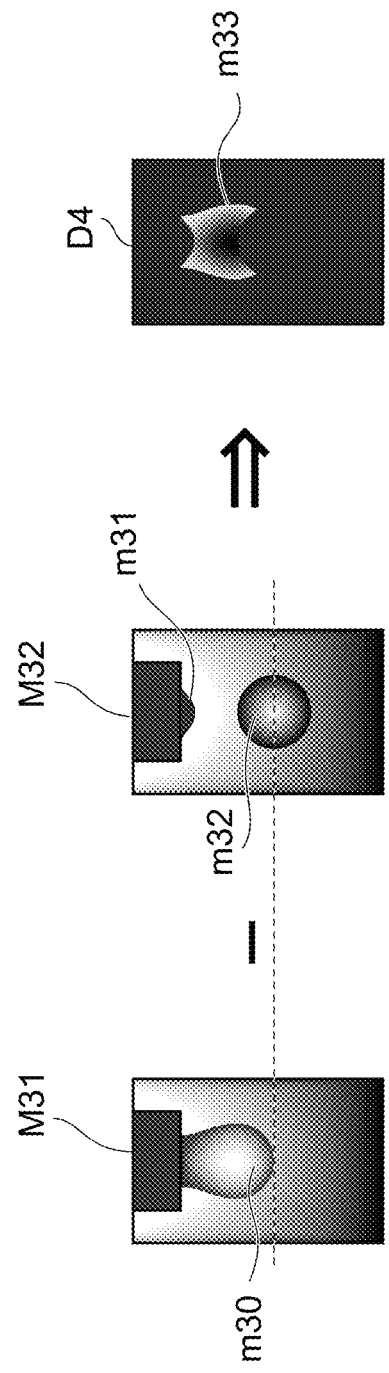
FIG. 15 is a schematic diagram for describing the droplet volume calculation processing in the fifth embodiment of the present invention.

In order to eliminate the influence of the droplets attached to the nozzle, etc. and the position displacement, etc. of the nozzle after starting infusion, it is possible to create, as shown in FIG. 14, a difference image between the image-immediately-before-dripping M31 and an image acquired from a frame close to this image-immediately-before-dripping M31. However, as shown in FIG. 15, the position of the liquid m30 hanging down from the nozzle in the image-immediately-before-dripping M31 and the position of the droplet m32 that has dripped down in the dripping-detected image M32 overlap one another between the image-immediately-before-dripping M31 and the dripping-detected image M32, which is the frame immediately thereafter, and thus, part of the liquid image m33 to be extracted in the difference image D4 between the two may be missing.

Figure 16:
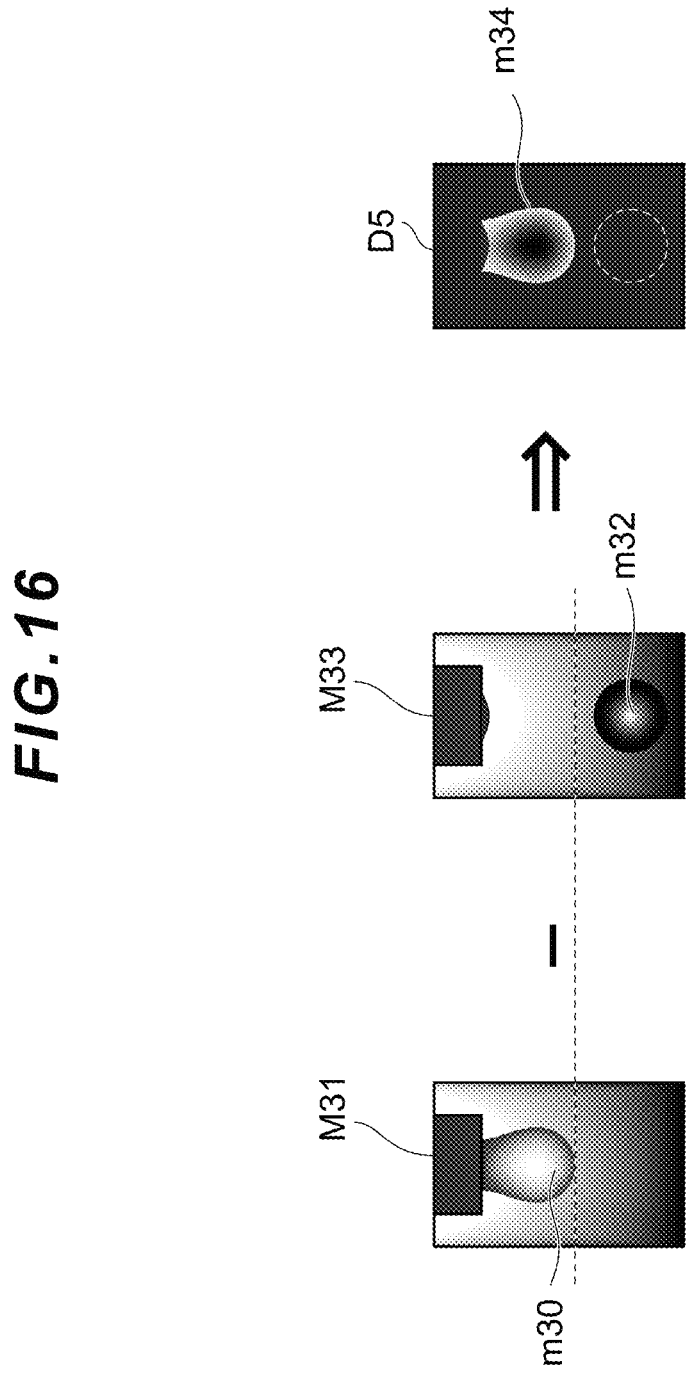
FIG. 16 is a schematic diagram for describing the droplet volume calculation processing in the fifth embodiment of the present invention.

Accordingly, in the present embodiment, the difference image is created using the image-immediately-after-dripping M33, which is an image acquired one frame after the dripping-detected image M32, as the reference image. Accordingly, as shown in FIG. 16, an almost complete liquid image m34 to be extracted can be extracted in the difference image D5 between the image-immediately-before-dripping M31 and the image-immediately-after-dripping M33. After generating the difference image D5, the binarization processing and the filling processing may be applied to the difference image D5, as with the first embodiment, and the volume may be calculated based on the area extracted from the binary image.

In this way, even when a long period of time has elapsed from the beginning of the infusion or even when the position or tilt of the nozzle has been displaced from the initial state, the volume of the droplets can be calculated with high precision according to the fifth embodiment of the present invention.

Example 5

An adult nozzle and an infant nozzle were used, the work distance was set as 28 mm, the infusion was performed with other conditions being similar to those of Example 1-1, and the volume of the droplets was calculated by way of the volume calculation processing in the fifth embodiment. Then, the following results were obtained when the error ratios were calculated in a manner similar to that of the above-described Example 1-1.

In the case of an adult nozzle and a work distance of 28 mm, and when the image-immediately-before-dripping and the image-immediately-after-dripping were used:
Dripping cycle 0.5 seconds/droplet: error ratio 1.16%
Dripping cycle 1.0 second/droplet: error ratio 0.74%
Dripping cycle 2.0 seconds/droplet: error ratio 0.37%

In the case of an infant nozzle and a work distance of 28 mm, and when the image-immediately-before-dripping and the image-immediately-after-dripping were used:
Dripping cycle 0.5 seconds/droplet: error ratio 0.94%
Dripping cycle 1.0 second/droplet: error ratio 0.25%
Dripping cycle 2.0 seconds/droplet: error ratio 1.27%

Based on the above-described experimental results, also in Example 5-1, it can be seen that, for both the adult nozzle and the infant nozzle, in all of the dripping cycles, good volume calculation precision can be obtained with a small error with respect to the real volume. In addition, results comparable to those of the above-described reference example can also be obtained.

Variation 5-1

Next, a variation of the fifth embodiment of the present invention will be described.

When the images obtained by the experiment using the infant nozzle in the above-described Example 5-1 were individually observed, there was a case where the positions of the liquid images overlap between the image-immediately-before-dripping and the image-immediately-after-dripping due to the fact that the dripping cycle was unstable with the infant nozzle and that the droplets occasionally dripped down sequentially. Therefore, the frame rate may be made variable such that the positions of the droplet images will not overlap between the image-immediately-before-dripping and the image-immediately-after-dripping (i.e. in a two-frame interval). For example, the operation unit 134 may be configured such that a user can arbitrarily adjust the frame rate (preferably in the range of 60 fps±10 fps) using the manipulation input unit 133 shown in FIG. 2 and that the imaging control unit 135 controls the operation of the camera 12 at the adjusted frame rate.

As an example of a method of adjusting the frame rate, in the case of the frame rate of 60 fps, when the image position of the liquid hanging down from the nozzle in the image-immediately-before-dripping and the image position the droplet dropping down in the image-immediately-after-dripping will partially overlap each other; however, when these image positions will not overlap each other between the image-immediately-before-dripping and the image acquired one frame after the image-immediately-after-dripping, the frame rate may be slightly reduced from 60 fps such that the imaging timing of the image-immediately-after-dripping will be reached when the droplet is dropped down slightly lower than the position of the liquid in the current image-immediately-after-dripping.

Variation 5-2

Figure 17:
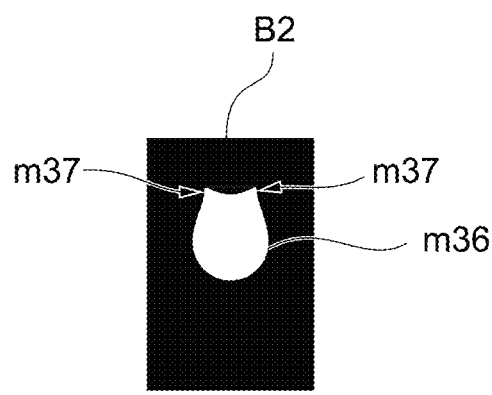
FIG. 17 is a schematic diagram for describing the droplet volume calculation processing in a variation of the fifth embodiment of the present invention.
Figure 18:
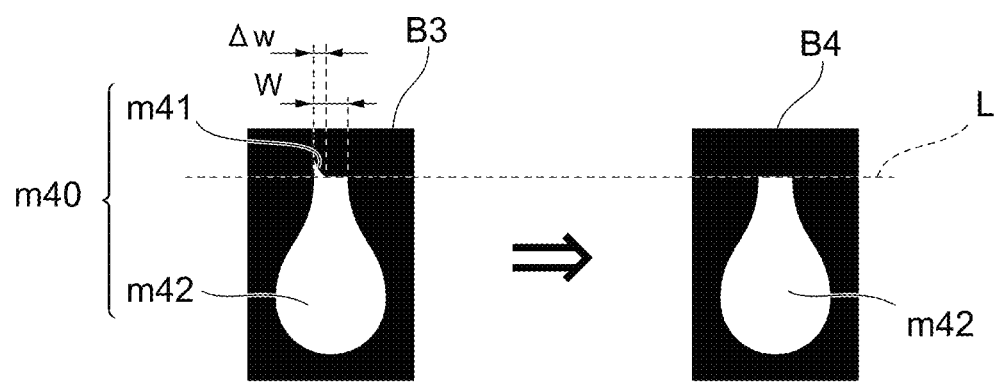
FIG. 18 is a schematic diagram for describing the droplet volume calculation processing in a variation of the fifth embodiment of the present invention.

Next, another variation of the fifth embodiment of the present invention will be described. FIGS. 17 and 18 are schematic diagrams for describing the droplet volume calculation processing in Variation 5-2.

As described in the fifth embodiment, when a difference image D5 is created between the image-immediately-before-dripping M31, in which the state where the liquid is hanging down from the nozzle is captured, and the image-immediately-after-dripping M33, in which the state where the liquid is remaining on the nozzle is captured, it is often the case that, as shown in FIG. 17, fragments m37 that project like horns appear at the upper part (the end part on the nozzle side) of the area m36 extracted from the binary image B2, which is obtained by applying the binarization processing and the filling processing to the difference image D5. When these fragments m37 appear symmetrically, such fragments m37 can be considered as the projection images of the body of revolution in a ring form having a hollow interior. Therefore, it is safe to consider that the volume of the body of revolution around the vertical axis of the entire extracted area m36 corresponds to the volume of a dropping droplet.

However, as shown in FIG. 18, a fragment m41 that projects asymmetrically may sometimes appear at the upper part of the area m40 extracted from the binary image B3. In this case, when the volume of the body of revolution around the vertical axis of the entire area m40 is calculated, despite the fragment m41 not being the projection image of the ring-like body of revolution, it may be treated as the ring-like body of revolution and then the volume may be calculated, and thus, it may be possible for there to be a large error with respect to the actual volume.

Accordingly, in the present Variation 5-2, the volume of the body of revolution is calculated after cutting off the fragment m41 that appears in the extracted area m40. More specifically, a flat line (i.e. a line corresponding to the lower end surface of the nozzle) L at the upper end of the area m40 is detected, and, as shown in the binary image B4, the volume of the body of revolution is calculated solely based on the part m42 of area m40, which is lower than the line L, and this is considered to be the volume of the droplet. The method of calculating the volume of the body of revolution is similar to the method described in the first embodiment (see FIG. 8).

As an example of the droplet volume calculation processing in the above-described Variation 5-2, an adult nozzle was used, the work distance was set as 28 mm, the infusion was performed with other conditions being similar to those of Example 1-1, and the volume of the droplets was calculated by way of the above-described processing. Then, the following results were obtained when the error ratios were calculated in a manner similar to that of the above-described Example 1-1.

In the case of an adult nozzle and a work distance of 28 mm, and when the fragment of the area extracted from the binary image was cut off:
Dripping cycle 0.5 seconds/droplet: error ratio 1.168%
Dripping cycle 1.0 second/droplet: error ratio 0.730%
Dripping cycle 2.0 seconds/droplet: error ratio 0.366%

On the other hand, when the volume of the droplet was calculated without cutting off the fragment of the area extracted from the binary image, and when the error ratios were calculated, the following results were obtained.

In the case of an adult nozzle and a work distance of 28 mm, and when the fragment of the area extracted from the binary image was not cut off:
Dripping cycle 0.5 seconds/droplet: error ratio 1.164%
Dripping cycle 1.0 second/droplet: error ratio 0.728%
Dripping cycle 2.0 seconds/droplet: error ratio 0.370%

The error in the calculated droplet volume between the case where the fragment of the area extracted from the binary image was processed to be cut off and the case where such processing was not performed, was on average approximately ±0.02 μL. Therefore, no significant difference was found in the error ratios regardless of whether the fragment was cut off based on the above-described experimental results. However, when the dripping cycle was long (1.0 second, 2.0 seconds), the variation in the calculated volume tended to be smaller when the fragment was cut off. Considering these experimental results, although whether to cut off the fragment will not have a significant influence on the precision of the volume calculation processing, it can be said that it is preferable to cut off the fragment from the perspective of volume calculation processing load.

Variation 5-3

Next, a further variation of the fifth embodiment of the present invention will be described, with reference to FIG. 18.

The processing of the fragment m41 in the area m40 extracted from the binary image B3 shown in FIG. 18 may be varied depending on the size of the fragment m41. For example, the width W of the area m40 on the line L at the upper end of the area m40 and the width Δw of the fragment m41 that projects upwardly from the line L may be detected, the ratio Δw/W of the width Δw of the fragment m41 with respect to the width W of the area m40 on the line L may be calculated, and the processing of the fragment m41 may be determined based on this ratio Δw/W.

More particularly, when the ratio Δw/W is below a predetermined threshold (for example, below 1/10-1/5), the fragment m41 is cut off, and then the volume of the body of revolution is calculated solely based on the part m42 of the area m40, which is below the line L and this volume is considered as the volume of the droplet. On the other hand, when the ratio Δw/W is equal to or larger than the threshold, both the volume of the body of revolution based on the part m42 of the area m40, which is below the line L, and the volume of the body of revolution based on the fragment m41 are calculated, and the sum of these volumes is considered as the volume of the droplet. The method of calculating the volume of each body of revolution is similar to the method described in the first embodiment (see FIG. 8). In addition, the volume of the body of revolution of the fragment m41 may also be calculated as the volume of a cone by assuming the width Δw as the diameter of the base.

Sixth Embodiment

Next, a sixth embodiment of the present invention will be described. The droplet measurement system and the droplet measurement method according to the sixth embodiment of the present invention are generally similar to those of the above-described first embodiment (see FIGS. 1 to 3), and the droplet volume calculation processing in step S13 in FIG. 3 differs from that of the first embodiment.

As described in the above-described Variation 5-1, as with the above-described fifth embodiment, when an infant nozzle is used for the infusion, the positions of the liquid images may overlap each other between the image-immediately-before-dripping and the image-immediately-after-dripping when the droplet volume is calculated based on the difference image between the image-immediately-before-dripping and the image-immediately-after-dripping. Therefore, the inventors of the present application considered using an image acquired one frame after the image-immediately-after-dripping (i.e. an image acquired two frames after the dripping-detected image) as the reference image, instead of the image-immediately-after-dripping. Hereinafter, an image acquired a predetermined number of frames after the dripping-detected image is also referred to as the image-after-dripping.

For the purpose set forth above, first, the infusion was performed using an infant nozzle under the same conditions, and then, the volume calculation processing was performed for each of the case where the image-immediately-before-dripping and the image-immediately-after-dripping were used and the case where the image-immediately-before-dripping and an image acquired two frames after the dripping-detected image were used. The volume calculation processing is similar to that of the fifth embodiment except that an image acquired two frames after the dripping-detected image may be used instead of the image-immediately-after-dripping. It should be noted that, generally, no asymmetrical fragment appeared in the area extracted from the binary image when an infant nozzle was used and thus, the volume was calculated on the assumption that there was no fragment.

The following results were obtained regarding the error ratios of the calculated volume with respect to the real volume.

In the case of an infant nozzle and a work distance of 28 mm, and when the image-immediately-before-dripping and the image-immediately-after-dripping were used:
Dripping cycle 0.5 seconds/droplet: error ratio 0.465%
Dripping cycle 1.0 second/droplet: error ratio 0.822%

Dripping cycle 2.0 seconds/droplet: error ratio 1.267%

In the case of an infant nozzle and a work distance of 28 mm, and when the image-immediately-before-dripping and an image acquired two frames after the dripping-detected image were used:

Dripping cycle 0.5 seconds/droplet: error ratio 1.383%
Dripping cycle 1.0 second/droplet: error ratio 0.081%
Dripping cycle 2.0 seconds/droplet: error ratio 1.528%

In terms of the above-described experimental results regarding the infant nozzle, no significant difference was found in the error ratios between the case where the image-immediately-after-dripping was used as the reference image and the case where the image acquired two frames after the dripping-detected image was used as the reference image. However, when the image-immediately-after-dripping was used as the reference image, the variation in the calculated volume was on the order of 2 μL and thus, was quite significant. In contrast, when the image acquired two frames after the dripping-detected image was used as the reference image, the variation in the calculated volume was suppressed. Considering these experimental results, although the situation may differ depending on the dripping cycles and the types of infusion liquid, it can be said that it is preferable to use an image acquired two frames after the dripping-detected image as the reference image when using an infant nozzle.

On the other hand, the infusion was performed in a similar manner with an adult nozzle and the volume calculation processing was performed for each of the case where the image-immediately-before-dripping and the image-immediately-after-dripping were used and the case where the image-immediately-before-dripping and an image acquired two frames after the dripping-detected image were used. The volume calculation processing is similar to that of the fifth embodiment except that an image acquired two frames after the dripping-detected image may be used instead of the image-immediately-after-dripping. However, the arithmetic load was reduced by uniformly performing the processing of cutting off the fragment as described above in Variation 5-2 on the area extracted from the binary image.

The following results were obtained regarding the error ratios of the calculated volume with respect to the real volume.

In the case of an adult nozzle and a work distance of 28 mm, and when the image-immediately-before-dripping and the image-immediately-after-dripping were used:

Dripping cycle 0.5 seconds/droplet: error ratio 1.168%
Dripping cycle 1.0 second/droplet: error ratio 0.730%
Dripping cycle 2.0 seconds/droplet: error ratio 0.366%

In the case of an adult nozzle and a work distance of 28 mm, and when the image-immediately-before-dripping and an image acquired two frames after the dripping-detected image were used:

Dripping cycle 0.5 seconds/droplet: error ratio 1.899%
Dripping cycle 1.0 second/droplet: error ratio 0.838%
Dripping cycle 2.0 seconds/droplet: error ratio 0.291%

In terms of the above-described experimental results regarding the adult nozzle, although the situation may differ depending on the dripping cycles, it can be said that it is generally preferable to use the image-immediately-after-dripping as the reference image.

Accordingly, the present embodiment may enable the image-after-dripping, which is to be used as the reference image, to be changed depending on the types of nozzles (adult, infant) to be used for the infusion, the types of infusion liquid and the infusion conditions, such as the dripping cycle, etc. For example, the operation unit 134 may be configured such that, when a user inputs the type of the nozzle and the infusion conditions, such as the dripping cycle, etc., using the manipulation input unit 133 shown in FIG. 2, the volume calculation unit 137c determines the image-after-dripping (i.e. the frame interval from the dripping-detected image) to be used as the reference image depending on the input infusion conditions, and performs the volume calculation processing by taking in the image-immediately-before-dripping and the determined image-after-dripping. The volume calculation processing performed by the volume calculation unit 137c is similar to that of the above-described fifth embodiment except that the image-after-dripping, which is acquired two frames after the dripping-detected image, may be used as the reference image.

Therefore, the sixth embodiment of the present invention enables the volume calculation processing to be executed using an appropriate image depending on the infusion conditions.

Variation 6-1

Next, a variation of the sixth embodiment of the present invention will be described.

The above-described sixth embodiment enabled the image-after-dripping, which is to be used as the reference image, to be changed depending on the types of nozzles used for the infusion; however, it may be preferable to communalize the volume calculation algorithms regardless of the nozzle type. In such case, even when the adult nozzle is used, it may be preferable to use the image acquired two frames after the dripping-detected image as the reference image in conformity with the infant nozzle.

Variation 6-2

Next, another variation of the sixth embodiment of the present invention will be described.

The frame rate may be made variable in order to obtain optimum arithmetic results depending on the nozzle type, while communalizing the volume calculation algorithms regardless of the nozzle used. In this case, the volume calculation algorithm uses the image (i.e. the image-after-dripping) acquired two frames after the dripping-detected image as the reference image, in conformity with the case when an infant nozzle is used. In the case where an adult nozzle is used, the frame rate may be slightly increased in the range such that the image position of the liquid hanging down from the nozzle in the image-immediately-before-dripping and the image position of the droplet dropping down in the image-after-dripping may not overlap each other in order to reduce the imaging timing gap between the image-immediately-before-dripping and the image-after-dripping.

Variation 6-3

Next, a further variation of the sixth embodiment of the present invention will be described.

The above-described sixth embodiment uniformly performed the processing of cutting off the fragment as described in Variation 5-2 on the area extracted from the binary image, which is based on the difference image between the image-immediately-before-dripping and the image-after-dripping. However, the fragment processing may be varied depending on the size of the fragment, as with Variation 5-3.

As described above, the respective embodiments and variations of the present invention calculate the volume of the droplet based on, at least, an image-before-dripping that captures therein the liquid hanging down from the nozzle and a reference image that is different from the image-before-dripping and that captures therein at least a tip part of a nozzle, and thus, the use of an imaging device can be dispensed with, which is provided with a large-sized, high-frame-rate imaging sensor capable of capturing the state in which droplets are dropping down from a nozzle in a time sequential manner. Accordingly, a system can be simply configured by combining a general-purpose imaging device, a general-purpose arithmetic processing device, and the like. Accordingly, mass production of the system may also be enabled.

In addition, the respective embodiments and variations of the present invention enable imaging to be performed at close range as compared to the case where the state in which the droplets are dropping down is captured, and thus, the volume of the droplet can be precisely calculated based on the image of the liquid captured in the image in a magnified manner. Moreover, since the invention images, at least, the liquid in the state of hanging down from the nozzle, the work distance, which is the distance between the imaging device and the subject, can be stabilized, and thus, the volume of the droplet can be precisely measured with good and stable precision.

The invention described heretofore is not limited to the above-described first to sixth embodiments and variations thereof, and various inventions may be formed by appropriately combining a plurality of components disclosed in the above-described first to sixth embodiments and variations thereof. For example, inventions may be formed by removing a few components from the entirety of the components shown in the above-described first to sixth embodiments and variations thereof, or by appropriately combining the components shown in the above-described embodiments and variations thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A droplet measurement system that measures the volume of a droplet dripping down from a nozzle, comprising:
   an imaging device configured to image a subject and output image data, wherein the imaging device is placed to locate an entire liquid hanging down from the nozzle at a tip part of the nozzle within a field of view;
   an image generation unit configured to generate, in a temporal sequential order, a plurality of images that capture a state in which droplets are dripping down from the nozzle based on an image data output from the imaging device;
   a dripping detection unit configured to detect an image indicating that a droplet has dripped from the nozzle from the plurality of images generated in a temporal sequential order by the image generation unit, which the plurality of images generated in a temporal sequential order include at least one image including an about-to-drip droplet hanging down from the nozzle tip part, which at least one image includes liquid which will become residual liquid hanging down from the nozzle tip part when the about-to-drip droplet has dripped, and at least one image in which the droplet no longer is hanging down from the nozzle tip part, thereby indicating the droplet has dripped, and the residual liquid from the droplet which has dripped is hanging down from the nozzle tip part; and
   a volume calculation unit configured to calculate the volume of the droplet which has dripped as a difference between volume of the about-to-drip droplet as determined from any one of the at least one image including the about-to-drip droplet and volume of the residual liquid as determined from any one of the at least one image in which the droplet no longer is hanging down from the nozzle tip part and the residual liquid from the droplet which has dripped is hanging down from the nozzle tip part.

2. The droplet measurement system according to claim 1, wherein
   the imaging device is placed to locate also the tip part of the nozzle within the field of view;
   the image generation unit is also configured to generate a base image of the nozzle tip part with no liquid clinging thereto;
   the droplet measurement system further comprises a storage unit configured to store the base image; and
   wherein the image including the about-to-drip droplet and the image in which the droplet no longer is hanging down from the nozzle tip part and residual liquid from the droplet which has dripped is hanging down from the nozzle tip part each include the nozzle tip part and the configuration of the volume calculation unit to calculate the volume of the droplet subtracts the base image in calculating the volume of the droplet.

3. The droplet measurement system according to claim 1, wherein
   the volume calculation unit is configured to calculate the volume of the droplet based on an image difference between the image of the about to drip droplet and the image in which the droplet no longer is hanging down form the nozzle tip part and residual liquid from the droplet which has dripped is hanging down from the nozzle tip part.

4. The droplet measurement system according to claim 3, wherein
   the volume calculation unit is configured to extract an area that captures the about-to-drip droplet by applying binarization processing to the difference between the image of the about-to-drip droplet and the image in which the droplet no longer is hanging down from the nozzle tip part and residual liquid from the droplet which has dripped is handing down from the nozzle tip part and to apply filling processing to an interior area of the area, and
   to calculate the volume of the droplet based on the interior area to which the filling processing is applied.

5. The droplet measurement system according to claim 3, wherein
   the volume calculation unit is configured to extract an area that captures liquid hanging down from the nozzle by applying binarization processing to the image difference, and,
   when a part projecting upwardly from a position corresponding to a lower end surface of the nozzle is asymmetrical in the extracted area, to calculate the volume of the droplet based on an area that remains after removing the part from the area.

6. The droplet measurement system according to claim 3, wherein
   the volume calculation unit is configured to extract an area that captures liquid hanging down from the nozzle by applying binarization processing to the difference image, when a part projecting upwardly from a position corresponding to a lower end surface of the nozzle is asymmetrical in the extracted area, to calculate a ratio of a width of the part projecting upwardly from the position with respect to a width of an area at the position corresponding to the lower end surface of the nozzle, when the ratio is below a predetermined value, the volume calculation unit is configured to calculate the volume of the droplet based on an area that remains after removing the part from the area, and when the ratio is equal to or larger than the predetermined value, the volume calculation unit is configured to calculate, as the volume of the droplet, a total value of the volume calculated based on the area that remains after removing the part from the area and the volume calculated based on the part.

7. The droplet measurement system according to claim 1, wherein
a frame rate of the imaging device is variable within a range of 60 frames per second±10 frames per second.

8. The droplet measurement system according to claim 1, wherein
the imaging device includes an imaging element having a number of pixels in a longer direction ranging from 480 to 800, inclusive, the number of pixels in a shorter direction ranging from 320 to 600, inclusive, and a total number of pixels being equal to or less than 500,000.

9. The droplet measurement system according to claim 1, wherein
the imaging device includes a telecentric lens.

10. The droplet measurement system according to claim 1, wherein
the nozzle is provided on an infusion device that infuses liquid filled in a container via a drip tube, and the nozzle drips down droplets made of the liquid into the drip tube, the system further comprising:
an actuator that varies a flow rate of the liquid by varying a pressing force on a tube that flows therein the liquid accumulated in the drip tube by driving a clamp that is provided in a pressable manner with respect to the tube; and
a flow rate control unit that controls the actuator such that the flow rate of the liquid is within a predetermined range based on the result of the volume calculation.

11. A droplet measurement method that measures the volume of a droplet dripping down from a nozzle, comprising:
generating, in a temporal sequential order, a plurality of images that capture a state in which droplets are dripping down from the nozzle based on image data output from an imaging device that is placed to locate an entire liquid hanging down from the nozzle at a tip part of the nozzle within a field of view;
detecting an image indicating that a droplet has dripped from the nozzle from the plurality of images that are generated in a temporal sequential order and that capture the state in which droplets are dripping down from the nozzle, which the plurality of images that are generated in a temporal sequential order include at least one image including an about-to-drip droplet hanging down from the nozzle tip part, which image includes liquid which will become residual liquid hanging down from the nozzle tip part when the about-to-drip droplet has dripped, and at least one image in which the droplet no longer is hanging down from the nozzle tip part, thereby indicating the droplet has dripped, and the residual liquid from the droplet which has dripped is hanging down from the nozzle tip part; and
calculating the volume of the droplet which has dripped as a difference between volume of the about-to-drip droplet as determined from any one of the at least one image including the about-to-drip droplet and volume of the residual liquid as determined from any one of the at least one image in which the droplet no longer is hanging down from the nozzle tip part and residual liquid from the droplet which has dripped is hanging down from the nozzle tip part.

12. A computer readable recording device that stores thereon a program for measuring the volume of a droplet dripping down from a nozzle, the program causing a computer to:
generate, in a temporal sequential order, a plurality of images that capture the state in which droplets are dripping down from the nozzle based on image data output from an imaging device that is placed to locate an entire liquid hanging down from the nozzle at a tip part of the nozzle within a field of view;
detect an image indicating that a droplet has dripped from the nozzle from the plurality of images that are generated in a temporal sequential order and that capture the state in which droplets are drip down from the nozzle, which the plurality of images that are generated in a temporal sequential order include at least one image including an about-to-drip droplet hanging down from the nozzle tip part, which image includes liquid which will become residual liquid hanging down from the nozzle tip part when the about-to-drip droplet has dripped, and at least one image in which the droplet no longer is hanging down from the nozzle tip part, thereby indicating the droplet has dripped, and the residual liquid from the droplet which has dripped is handing down from the nozzle tip part; and
calculate the volume of the droplet which has dripped as a difference between volume of the about-to-drip droplet as determined from any one of the at least one image including the about-to-drip droplet and volume of the residual liquid as determined from any one of the at least one image in which the droplet no longer is hanging down from the nozzle tip part and residual liquid from the droplet which has dripped is hanging down from the nozzle tip part.

13. The droplet measurement system according to claim 1, wherein the image including the about-to-drip droplet used in the volume calculation unit is an image generated one frame before the first detected image among the pt least one image in which the droplet no longer is hanging down from the nozzle tip part and residual liquid from the droplet which has dripped is hanging down from the nozzle tip part.

14. The droplet measurement system according to claim 2, wherein the volume calculation unit is configured to calculate the volume of the about-to-drip droplet based on an image difference between the image of the about-to-drip droplet and the base image, and to calculate the volume of the residual liquid based on an image difference between the image in which the droplet no longer is hanging down from the nozzle tip part and residual liquid from the droplet which has dripped is hanging down from the nozzle tip part and the base image.

* * * * *